(12) United States Patent
Moneymaker et al.

(10) Patent No.: US 9,549,982 B2
(45) Date of Patent: Jan. 24, 2017

(54) ULTRA LOW DOSE NUTRACEUTICAL COMPOSITIONS FOR ENHANCING SLEEP QUALITY AND TREATING SLEEP DISORDERS

(75) Inventors: Ricky Dean Moneymaker, Stuarts Draft, VA (US); Larry S. Klesman, Lake Forest, IL (US); Jon S. Theus, Gurnee, IL (US)

(73) Assignee: Foundational Biosystems, LLC, Riverwoods, IL (US)

( * ) Notice: Subject to any disclaimer, the term of this patent is extended or adjusted under 35 U.S.C. 154(b) by 435 days.

(21) Appl. No.: 12/949,340

(22) Filed: Nov. 18, 2010

(65) Prior Publication Data

US 2011/0123507 A1 May 26, 2011

Related U.S. Application Data

(60) Provisional application No. 61/263,437, filed on Nov. 23, 2009.

(51) Int. Cl.
| | |
|---|---|
| *A23L 33/10* | (2016.01) |
| *A61K 45/06* | (2006.01) |
| *A61K 31/122* | (2006.01) |
| *A61K 33/14* | (2006.01) |

(52) U.S. Cl.
CPC ............. *A61K 45/06* (2013.01); *A23L 33/15* (2016.08); *A23L 33/155* (2016.08); *A23L 33/16* (2016.08); *A23L 33/175* (2016.08); *A61K 31/122* (2013.01); *A61K 33/14* (2013.01); *A23V 2002/00* (2013.01); *A23V 2250/0618* (2013.01)

(58) Field of Classification Search
CPC ....................................................... A23L 33/10
See application file for complete search history.

(56) References Cited

U.S. PATENT DOCUMENTS

2007/0104762 A1* 5/2007 Roizen ..................... A23G 3/34
424/439

OTHER PUBLICATIONS

Norman, "From vitamin D to hormone D: fundamentals of the vitamin D endocrine system essential for good health," Am J Clin Nutr 88(suppl):491S-499S, 2008.*

* cited by examiner

*Primary Examiner* — Rosanne Kosson
(74) *Attorney, Agent, or Firm* — David G. Rosenbaum; J. Peter Paredes; Rosenbaum IP, P.C.

(57) ABSTRACT

The present technology relates to a dietary supplement, composition, nutraceutical, and/or system for inducing or treating biological responses or conditions (namely sleep or sleep disorders) which utilize ultra-low dosage amounts of vitamins, minerals, amino acids, co-enzymes, stimulants, and/or similar ingredients in a highly bio-active delivery system which bypasses first pass metabolism. In particular, the present technology relates to a nutraceutical composition/formulation which substantially bypasses first pass metabolism and such as, but not limited to, sleep apnea. Methods of using the composition/formulation to elicit enhanced sleep quality, induce short duration sleep and/or treat sleep disorders are also provided.

17 Claims, 20 Drawing Sheets

ULTRA LOW DOSE NUTRACEUTICAL COMPOSITIONS FOR ENHANCING SLEEP QUALITY AND TREATING SLEEP DISORDERS

RELATED APPLICATIONS

This application claims priority to and benefit from U.S. Provisional Patent Application Ser. No. 61/263,437, filed on Nov. 23, 2009, the content of which is herein incorporated by reference in its entirety.

FIELD OF THE INVENTION

The present technology relates generally to individualized responsive dosing dietary supplement systems, compositions, methods of treatment, and processes of producing the same, which allow a consumer or patient to target identifiable, individualistic biological conditions or responses. More specifically, the present technology relates to a dietary supplement, composition, nutraceutical, and/or system for targeting individualized biological conditions or responses (namely sleep, different forms of sleep, or sleep disorders) which utilize ultra-low dosage amounts of vitamins, minerals, amino acids, co-enzymes, stimulants, and/or similar ingredients in a highly bio-active delivery system, such that an individual may take multiple doses of the same or different dietary supplement mixture based on varying biological need or desired response within each 24 hour period. In particular, the present technology relates to a nutraceutical/supplement composition for enhancing sleep quality and/or treating sleep disorders such as, but not limited to, sleep apnea.

BACKGROUND

Vitamins, minerals, amino acids, and co-enzymes are compounds required by an animal or human body in small amounts for metabolism, biophysiological repair, to protect health, and for proper growth and cellular reproduction. These compounds also assist in the formation of hormones, blood cells, nervous-system chemicals, and genetic material. Vitamins, minerals, amino acids, and co-enzymes are often referred to as nutrients, defined herein as a substance or ingredient which may be found in food which imparts a medicinal or health benefit. The various nutrient compounds are not chemically related, and most differ in their physiological actions. They generally act as catalysts, combining with proteins to create metabolically active enzymes that in turn produce hundreds (or more) of important chemical reactions throughout the body. Without nutrients, many of these reactions would slow down or cease. The intricate ways in which nutrients act on the body (e.g., positive and negative feedback regulatory processes), however, are still far from clear.

Dietary supplements are generally nutrient mixtures commonly taken in single mega-dose dosage forms which contain vitamin, mineral and other nutrient doses. Although mega-dose regimens are a common practice for the prevention of disease, there is a great deal of debate in the conventional literature regarding the efficacy of such regimens. Moreover, consuming large doses of vitamins, minerals, or other nutrients, in the absence of some deficiency or without proper medical supervision, may cause harmful toxic effects and/or result in hypervitaminosis.

Additionally, a consumer usually has little choice in choosing the variety of ingredients, dosage levels, or dosing regimens of a conventional dietary supplement, such as a standard vitamin tablet. Conventional dietary supplements may be effective for a general purpose, but can provide an excess of vitamins, minerals, stimulants, or other compounds which a consumer does not desire, or those supplements may not adequately target an individual's specific dietary need or desired biological response. Additionally, conventional dosage forms of dietary supplements only allow a consumer to take one or two doses per 24 hour period. As a result, conventional dietary supplements fail to recognize that the physiological state and resultant nutrient requirements of any single individual can depend upon and fluctuate based upon a number of different biophysical variables during the course of each day or dosing regimen. For example, individual variations in diet, and the amount and intensity of physical activity, provide physical and chemical stimuli that stress various systems of the body to differing degrees from one person to the next and for each of those individuals on any given day. Thus, standard "one size fits all" mega-dose dosage forms/regimens are not amenable to empirical dosage adjustment to achieve an individualized biophysiological objective or response such as, but not limited to, enhanced sleep quality, initiation of sleep, sleep maintenance, and the like.

Another drawback with most conventional dietary supplements is that they suffer from poor degrees and/or rates at which the various nutrients are absorbed into the systemic circulation of the body and made available for biophysiological activity (e.g., "bioavailability"). These degrees or rates of bioavailability typically depend upon the dose, dosage form, and method of administration.

One particular barrier to efficient nutrient bioavailability is "first-pass metabolism", which is defined herein to mean a process in which the nutrient compound(s) are modified, activated, or inactivated before they enter the systemic circulation, or are left unchanged and excreted. Alternatively, it may be defined as the intestinal and hepatic degradation or alteration of a drug or substance taken by mouth, after absorption, removing some of the active substance or nutrient from the blood before it enters the general circulation.

For example, it is generally understood by those skilled in at least the nutraceutical and/or supplements field that one significant drawback to "mega-dosing" of vitamins and minerals is that increased dosages may not be adequately absorbed into the body, or may actually decrease absorption. Thus, available transport mechanisms may become saturated and unable to absorb the excess dose of the vitamin, mineral, or other nutrient. Additionally, a drawback to vitamin or mineral delivery via a conventional tablet or capsule is that differences in luminal pH along the gastrointestinal tract lining, surface area per luminal volume, blood perfusion, presence of bile and mucus, and the nature of epithelial membranes may prevent or alter efficient absorption, activation, and the like of a nutrient, thereby decreasing its bioavailability and subsequent usage by the human body.

To compensate for first pass metabolism effects, some previous efforts have been directed to enterically coated tablet or capsule dosage forms which pass through the stomach unaltered to disintegrate in the lower intestines. However, aside from a delayed biophysiological response as gastric emptying becomes rate-limiting, gastric irritability, and potential allergic reactions from the ingestion of such coating materials occurs, and these enterically coated delayed release dosage forms dissolve and are absorbed within a narrow time frame. As a result, the body typically excretes the non-absorbed vitamins or minerals.

Additional previous attempts in addressing the challenge of bypassing first pass metabolism have been directed to continuous or gradual release dosage forms. U.S. Pat. No. 4,882,167, to Jang, discloses dry direct compressed products for controlled release of actives including vitamins or minerals. However, there still remains the challenge of a composition having ultra-low dosage amounts of vitamins or minerals, dosing flexibility, or alternatively systems, compositions, or methods for individualized responsive dosing based on at least one desired biological response such as increased sleep quality or treatment of a sleep disorder.

WO 99/17753 (to Awamura et al.) discloses rapidly dissolving films for delivery of drugs to be adsorbed in the digestive tract. U.S. Pat. No. 6,596,298, to Leung, discloses consumable oral care films which may optionally contain active amounts of pharmaceutical drugs. However, there still remains the challenge of utilizing vitamins or minerals, and more specifically, ultra-low dosage amounts of nutrients which would operate to provide flexibility for individualized dosing, especially in the promotion, enhancement or improvement in sleep initiation, maintenance, and/or quality. Moreover, these products or processes do not provide a system or selection for varying the type or level of dosage depending on a biological response desired, such as a focus upon sleep.

Therefore, there is presently a need for an efficient process for producing a nutrient dosage and delivery system that is capable of individualized biological response dosing (i.e., dosing based upon empirical analysis and adjustment in response to a desired biological outcome such as enhanced sleep quality and the like), which is available in a suitable dosage form, and preferably is efficiently absorbed and made bioavailable to animal or human tissue. Additionally, there is presently a need for a treatment method for managing finely tuned biological needs and responses which utilizes ultra low dosage amounts, substantially avoids first pass metabolism, and allows for varied dosage/dosing regimens within each dosing period (e.g., 24 hours, 6 hours, 1 hour). Furthermore, there exists a present need for an ultra low dose nutraceutical that substantially avoids first pass metabolism and which enhances sleep quality and/or can be used to treat sleep disorders including, but not limited to, sleep apnea.

SUMMARY OF THE INVENTION

In at least one aspect, the present technology provides a nutraceutical composition comprising at least two of the following in a single dose volume of about 0.25 milliliters: about $5.45 \times^{-7}$ g magnesium chloride; about $8.17 \times^{-7}$ g sodium ascorbate; about $8.17 \times^{-7}$ g potassium carbonate; about $5.45 \times^{-7}$ g calcium ascorbate; about $4.54 \times^{-6}$ g ascorbic acid (ester C); about $8.62 \times^{-7}$ g caffeine; about $9.08 \times^{-8}$ g niacin; about $4.08 \times^{-7}$ g potassium benzoate; about $1.70 \times^{-9}$ g chromium picolinate; about $1.70 \times^{-9}$ g chromium polynicotinate; about $5.67 \times^{-7}$ g coenzyme Q-10; about $2.27 \times^{-6}$ g L-glutamine; about $2.27 \times^{-6}$ g L-arginine; about $9.08 \times^{-7}$ g potassium sorbate; about $6.58 \times^{-7}$ g sodium nitrite; about $9.36 \times^{-8}$ g vitamin A; about $1.64 \times^{-9}$ g vitamin B1; about $1.24 \times^{-9}$ g vitamin B2; about $1.58 \times^{-8}$ g vitamin B3; about $1.58 \times^{-8}$ g vitamin B6; about $4.73 \times^{-12}$ g vitamin B12; about $4.73 \times^{-8}$ g vitamin C; about $7.48 \times^{-9}$ g vitamin D3; about $5.46 \times^{-10}$ g vitamin E; about $1.42 \times^{-10}$ g vitamin H; about $1.51 \times^{-10}$ g folic acid; about $6.93 \times^{-10}$ g copper; about $6.02 \times^{-9}$ g iron; about $5.18 \times^{11}$ g potassium iodide; about $3.15 \times^{-8}$ g calcium carbonate; or about $5.07 \times^{-9}$ g zinc.

In another aspect, a nutraceutical composition of the present technology is provided to an individual to induce enhanced sleep quality in the individual. The enhanced sleep quality outcomes of the present technology may be characterized by an outcome selected from the group consisting essentially of decreased ratio of stage 1 sleep to DELTA sleep, decreased ratio of stage 1 sleep to REM sleep, decreased number of awakenings, decreased number of arousals, decreased latencies, increased levels of blood oxygen saturation, and a decreased number of sleep disorder events. The decreased number of sleep disorder event outcomes of the present technology may be a decreased number of apneaic events.

In an additional aspect, a nutraceutical composition of the present technology may function to induce enhanced sleep quality through a non-systemic, central mechanism.

In a further aspect, a nutraceutical composition of the present technology is provided to an individual via an administration route that substantially avoids first pass metabolism. An administration route of the present technology may be selected from the group consisting essentially of sublingual, buccal, nasal, transdermal, intradermal, intramuscular, intravenous and rectal routes.

In certain aspects, a nutraceutical composition of the present technology may further comprise at least one additive. Additives that are compatible with the present technology may be present in amounts from about $2 \times 10^{-14}$ grams to about $1.5 \times 10^{-2}$ grams of at least one dose of the nutraceutical.

In additional aspects, a nutraceutical composition of the present technology may be provided in a dosage form selected from the group consisting of parenteral, sublingual liquid, oral film, liquid, lozenge, ampoule, troche, suppository, transdermal patch, nasal spray, dragee, slurry, suspension, emulsion, injectable, and intravenous solution.

In another aspect, the present technology provides a method of improving sleep quality or treating a sleep disorder comprising administering a nutraceutical composition of the present technology. The method of improving sleep quality or treating a sleep disorder of the present technology may be characterized by an outcome selected from the group consisting of decreased ratio of stage 1 to DELTA sleep, decreased ratio of stage 1 to REM sleep, decreased number of apneas, decreased apnea index, decreased number of arousals, decreased arousal index, decreased number of awakenings, and increased levels of blood oxygen saturation.

In an additional aspect, the method of improving sleep quality or treating a sleep disorder of the present technology is achieved by administering a nutraceutical composition of the present technology to a subject in need thereof in a volume of about 0.25 milliliters.

In a further aspect, the method of improving sleep quality or treating a sleep disorder of the present technology is achieved by administering a nutraceutical composition of the present technology to a subject in need thereof in a volume of about 0.30 milliliters.

In at least one additional aspect, the present technology provides a nutraceutical composition comprising at least two of the following in a single dose volume of about 0.25 milliliters: about $3.61 \times^{-7}$ g magnesium chloride; about $5.42 \times^{-7}$ g sodium ascorbate; about $5.42 \times^{-7}$ g potassium carbonate; about $3.61 \times^{-7}$ g calcium ascorbate; about $3.01 \times^{-6}$ g ascorbic acid (ester C); about $5.72 \times^{-7}$ g caffeine; about $6.02 \times^{-8}$ g niacin; about $2.71 \times^{-7}$ g potassium benzoate; about $1.13 \times^{-9}$ g chromium picolinate; about $1.13 \times^{-9}$ g chromium polynicotinate; about $3.76 \times^{-7}$ g coenzyme Q-10; about $1.51 \times^{-6}$ g L-glutamine; about $1.51 \times^{-6}$ g L-arginine; about $6.02 \times^{-7}$ g potassium sorbate; about $4.37 \times^{-7}$ g sodium nitrite;

about $6.21\times^{-8}$ g vitamin A; about $1.09\times^{-9}$ g vitamin B1; about $8.20\times^{-10}$ g vitamin B2; about $1.05\times^{-8}$ g vitamin B3; about $1.05\times^{-8}$ g vitamin B6; about $3.14\times^{-12}$ g vitamin B12; about $3.14\times^{-8}$ g vitamin C; about $4.97\times^{-9}$ g vitamin D3; about $3.62\times^{-10}$ g vitamin E; about $9.41\times^{11}$ g vitamin H; about $1.00\times^{-10}$ g folic acid; about $4.60\times^{-10}$ g copper; about $3.99\times^{-9}$ g iron; about $3.44\times^{11}$ g potassium iodide; about $2.09\times^{-8}$ g calcium carbonate; or about $3.37\times^{-9}$ g zinc.

In a further aspect, a nutraceutical composition of the present technology may be provided to an individual to induce short duration sleep. The induced short duration sleep of the present technology may last for about one hour or less.

In another aspect, the present technology provides a nutraceutical composition comprising at least two of the following in a single dose volume of about 0.25 milliliters: about $9.11\times^{-8}$ g magnesium chloride; about $1.37\times^{-7}$ g sodium ascorbate; about $1.37\times^{-7}$ g potassium carbonate; about $9.11\times^{-8}$ g calcium ascorbate; about $7.59\times^{-7}$ g ascorbic acid (ester C); about $1.44\times^{-7}$ g caffeine; about $1.52\times^{-8}$ g niacin; about $6.84\times^{-8}$ g potassium benzoate; about $2.84\times^{-10}$ g chromium picolinate; about $2.84\times^{-10}$ g chromium polynicotinate; about $9.49\times^{-8}$ g coenzyme Q-10; about $3.80\times^{-7}$ g L-glutamine; about $3.80\times^{-7}$ g L-arginine; about $1.52\times^{-7}$ g potassium sorbate; about $1.10\times^{-7}$ g sodium nitrite; about $1.57\times^{-8}$ g vitamin A; about $2.74\times^{-10}$ g vitamin B1; about $2.07\times^{-10}$ g vitamin B2; about $2.64\times-9$ g vitamin B3; about $2.64\times-9$ g vitamin B6; about $7.91\times^{-13}$ g vitamin B12; about $7.91\times^{-9}$ g vitamin C; about $1.25\times^{-9}$ g vitamin D3; about $9.13\times^{11}$ g vitamin E; about $2.37\times^{11}$ g vitamin H; about $2.53\times^{11}$ g folic acid; about $1.16\times^{-10}$ g copper; about $1.01\times^{-9}$ g iron; about $8.66\times^{-12}$ g potassium iodide; about $5.27\times^{-9}$ g calcium carbonate; or about $8.49\times^{-10}$ g zinc.

In an additional aspect, the present technology provides a nutraceutical composition comprising at least two of the following in a single dose volume of about 0.25 milliliters: about $6.08\times^{-8}$ g magnesium chloride; about $9.12\times^{-8}$ g sodium ascorbate; about $9.12\times^{-8}$ g potassium carbonate; about $6.08\times^{-8}$ g calcium ascorbate; about $5.07\times^{-7}$ g ascorbic acid (ester C); about $9.63\times^{-8}$ g caffeine; about $1.01\times^{-8}$ g niacin; about $4.56\times^{-8}$ g potassium benzoate; about $1.89\times^{-10}$ g chromium picolinate; about $1.89\times^{-10}$ g chromium polynicotinate; about $6.33\times^{-8}$ g coenzyme Q-10; about $2.53\times^{-7}$ g L-glutamine; about $2.53\times^{-7}$ g L-arginine; about $1.01\times^{-7}$ g potassium sorbate; about $7.35\times^{-8}$ g sodium nitrite; about $1.04\times^{-8}$ g vitamin A; about $1.83\times^{-10}$ g vitamin B1; about $1.38\times^{-10}$ g vitamin B2; about $1.76\times^{-9}$ g vitamin B3; about $1.76\times^{-9}$ g vitamin B6; about $5.28\times^{-13}$ g vitamin B12; about $5.28\times^{-9}$ g vitamin C; about $8.36\times^{-10}$ g vitamin D3; about $6.09\times^{11}$ g vitamin E; about $1.58\times^{11}$ g vitamin H; about $1.69\times^{11}$ g folic acid; about $7.74\times^{11}$ g copper; about $6.72\times^{-10}$ g iron; about $5.78\times^{-12}$ g potassium iodide; about $3.52\times^{-9}$ g calcium carbonate; or about $5.66\times^{-10}$ g zinc.

In an additional aspect, the present technology provides a nutraceutical composition comprising at least five vitamins or minerals; wherein at least one dose of the nutraceutical comprises from about $1.25\times10^{-13}$ grams to about $3.5\times10^{-3}$ grams of at least one mineral, from about $6\times10^{-9}$ grams to about $6\times10^{-6}$ grams of at least one enzyme, from about $2\times10^{-14}$ grams to about $1.8\times10^{-4}$ grams of at least one vitamin, from about $3\times10^{-8}$ grams to about $3\times10^{-4}$ grams of at least one adjunct, and from about $1.5\times10^{-8}$ grams to about $1.5\times10^{-2}$ grams of at least one amino acid; wherein the nutraceutical/supplement composition is provided to an individual via an administration route that substantially avoids first pass metabolism; and wherein the nutraceutical/supplement composition is provided to an individual to induce enhanced sleep quality or sleep quality outcomes in the individual.

In another aspect, the present technology provides a nutraceutical/supplement composition comprising at least five vitamins or minerals; wherein at least one dose of the nutraceutical/supplement composition comprises from about $3\times10^{-8}$ grams to about $3\times10^{-4}$ grams of at least one stimulant, from about $1.25\times10^{-13}$ grams to about $3.5\times10^{-3}$ grams of at least one mineral, from about $6\times10^{-9}$ grams to about $6\times10^{-6}$ grams of at least one enzyme, from about $2\times10^{-14}$ grams to about $1.8\times10^{-4}$ grams of at least one vitamin, and from about $1.5\times10^{-8}$ grams to about $1.5\times10^{-2}$ of at least one amino acid; wherein the nutraceutical/supplement composition is provided to an individual via an administration route that substantially avoids first pass metabolism; and wherein the nutraceutical/supplement composition is provided to an individual to induce decreased sleep latency time and/or increased sleep time duration in the individual.

In a further aspect, the present technology provides a nutraceutical/supplement composition comprising at least five vitamins or minerals; wherein at least one dose of the nutraceutical/supplement comprises from about $1.25\times10^{-13}$ grams to about $3.5\times10^{-3}$ grams of at least one mineral, from about $6\times10^{-9}$ grams to about $6\times10^{-6}$ grams of at least one enzyme, from about $2\times10^{-14}$ grams to about $1.8\times10^{-4}$ grams of at least one vitamin, from about $3\times10^{-8}$ grams to about $3\times10^{-4}$ grams of at least one adjunct, and from about $1.5\times10^{-8}$ grams to about $1.5\times10^{-2}$ grams of at least one amino acid; wherein the nutraceutical/supplement is provided to an individual via an administration route that substantially avoids first pass metabolism; and wherein the nutraceutical/supplement is provided to an individual to treat a sleep disorder, for example, sleep apnea.

In an additional aspect, the present technology provides a method of improving sleep quality or treating a sleep disorder comprising administering a nutraceutical/supplement composition comprising at least five vitamins or minerals to an individual; wherein at least one dose of the nutraceutical/supplement comprises from about $3\times10^{-8}$ grams to about $3\times10^{-4}$ grams of at least one stimulant, from about $1.25\times10^{-13}$ grams to about $3.5\times10^{-3}$ grams of at least one mineral, from about $6\times10^{-9}$ grams to about $6\times10^{-6}$ grams of at least one enzyme, from about $2\times10^{-14}$ grams to about $1.8\times10^{-4}$ grams of at least one vitamin, and from about $1.5\times10^{-8}$ grams to about $1.5\times10^{-2}$ grams of at least one amino acid; wherein the nutraceutical/supplement is provided to the individual via an administration route that substantially avoids first pass metabolism; wherein the enhanced sleep quality or sleep disorder treatment is characterized by an outcome such as, but not limited to decreased ratio of stage 1 to DELTA sleep, decreased ratio of stage 1 to REM sleep, decreased number of apneas, decreased apnea index, decreased number of arousals, decreased arousal index, decreased number of awakenings, and increased levels of blood oxygen saturation; and wherein the nutraceutical/supplement functions to induce the sleep related outcome through a non-systemic, central mechanism.

In another aspect, the present technology provides a nutraceutical/supplement composition comprising at least five vitamins or minerals; wherein at least one dose of the nutraceutical/supplement composition comprises magnesium chloride, sodium ascorbate, potassium carbonate, calcium ascorbate, potassium sorbate, sodium nitrite, potassium benzoate, chromium picolinate, chromium polynicotinate, copper, iron, potassium iodide, calcium carbonate, zinc, ascorbic acid, niacin, vitamin A, vitamin B1, vitamin B2, vitamin B3, vitamin B6, vitamin B12, vitamin C, vitamin D3, vitamin E, vitamin H, folic acid, caffeine, co-enzyme Q-10, l-arginine, l-glutamine, and combinations and derivatives thereof; wherein the nutraceutical/supplement is provided to an individual via an administration route that substantially avoids first pass metabolism; and wherein the nutraceutical/supplement is provided to an individual to induce enhanced sleep quality in the individual.

In yet another aspect, the present invention provides a nutraceutical/supplement composition for enhancing sleep quality and/or treating a sleep disorder (e.g., sleep apnea, interrupted sleep, difficult sleep initiation, sleep latency disorder, among others); wherein at least one dose of the nutraceutical comprises from about $8.65824 \times -8$ grams to about $9.56963 \times^{-8}$ grams of magnesium chloride, from about $1.29874 \times^{-7}$ grams to about $1.43544 \times^{-7}$ grams of sodium ascorbate, from about $1.29874 \times^{-7}$ grams to about $1.43544 \times^{-7}$ grams potassium carbonate, from about $8.65824 \times^{-8}$ grams to about $9.56963 \times^{-8}$ grams of calcium ascorbate, from about $7.2152 \times^{-7}$ grams to about $7.97469 \times^{-7}$ grams of ascorbic acid (ester C), from about $1.37089 \times^{-7}$ grams to about $1.51519 \times^{-7}$ grams of caffeine, from about $1.44304 \times -8$ grams to about $1.59494 \times^{-8}$ grams of niacin, from about $6.49368 \times -8$ grams to about $7.17722 \times -8$ grams of potassium benzoate, from about $2.69848 \times^{-10}$ to about $2.98254 \times^{-10}$ grams of chromium picolinate, from about $2.69848 \times^{-10}$ grams to about $2.98254 \times^{-10}$ grams of chromium polynicotinate, from about $9.019 \times -8$ grams to about $9.96837 \times^{-8}$ grams of coenzyme Q10, from about $3.6076 \times^{-7}$ grams to about $3.98735 \times^{-7}$ grams of L-glutamine, from about $3.6076 \times^{-7}$ grams to about $3.98735 \times^{-7}$ grams L-arginine, from about $1.44304 \times^{-7}$ grams to about $1.59494 \times^{-7}$ grams of potassium sorbate, from about $1.0462 \times^{-7}$ grams to about $1.15633 \times^{-7}$ grams of sodium nitrite, from about $1.48762 \times^{-8}$ grams to about $1.64421 \times^{-8}$ grams of vitamin A, from about $2.60048 \times^{-10}$ to about $2.87421 \times^{-10}$ grams of vitamin B1, from about $1.96414 \times^{-10}$ grams to about $2.17089 \times^{-10}$ grams of vitamin B2, from about $2.50528 \times^{-9}$ grams to about $2.76899 \times^{-9}$ grams of vitamin B3, from about $2.50528 \times^{-9}$ grams to about $2.76899 \times^{-9}$ grams of vitamin B6, from about $7.51583 \times^{-13}$ grams to about $8.30697 \times^{-13}$ grams of vitamin B12, from about $7.51583 \times^{-9}$ grams to about $8.30697 \times^{-9}$ grams of vitamin C, from about $1.19009 \times^{-9}$ grams to about $1.31537 \times^{-9}$ grams of vitamin D3, from about $8.67776 \times^{11}$ grams to about $9.59121 \times^{11}$ grams of vitamin E, from about $2.25475 \times^{11}$ grams to about $2.49209 \times^{11}$ grams of vitamin H, from about $2.40507 \times^{11}$ grams to about $2.65823 \times^{11}$ grams of folic acid, from about $1.10232 \times^{-10}$ grams to about $1.21836 \times^{-10}$ grams of copper, from about $9.57016 \times^{-10}$ grams to about $1.05775 \times^{-9}$ grams of iron, from about $8.23016 \times^{-12}$ grams to about $9.0965 \times^{-12}$ grams of potassium iodide, from about $5.01055 \times^{-9}$ grams to about $5.53798 \times -9$ grams of calcium carbonate, and from about $8.06699 \times^{-10}$ grams to about $8.91615 \times^{-10}$ grams of zinc; and wherein the nutraceutical/supplement composition is provided to an individual via an administration route that substantially avoids first pass metabolism.

In a further aspect, the present technology provides a nutraceutical/supplement composition for enhancing short-time duration sleep; wherein at least one dose of the nutraceutical/supplement composition comprises from about $5.77505 \times^{-8}$ grams to about $6.38294 \times^{-8}$ grams of magnesium chloride, from about $8.66257 \times^{-8}$ grams to about $9.57442 \times^{-8}$ grams of sodium ascorbate, from about $8.66257 \times^{-8}$ grams to about $9.57442 \times^{-8}$ grams of potassium carbonate, from about $5.77505 \times -8$ grams to about $6.38294 \times^{-8}$ grams of calcium ascorbate, from about $4.81254 \times^{-7}$ grams to about $5.31912 \times^{-7}$ grams of ascorbic acid (also known as ester C), from about $9.14382 \times^{-8}$ grams to about $1.01063 \times^{-7}$ grams of caffeine, from about $9.62508 \times^{-9}$ grams to about $1.06382 \times^{-8}$ grams of niacin, from about $4.33128 \times^{-8}$ grams to about $4.78721 \times^{-8}$ grams of potassium benzoate, from about $1.79989 \times^{-10}$ grams to about $1.98935 \times^{-10}$ grams of chromium picolinate, from about $1.79989 \times^{-10}$ grams to about $1.98935 \times^{-10}$ grams of chromium polynicotinate, from about $6.01567 \times^{-8}$ grams to about $6.6489 \times^{-8}$ grams of coenzyme Q10, from about $2.40627 \times^{-7}$ grams to about $2.65956 \times^{-7}$ grams of L-glutamine, from about $2.40627 \times^{-7}$ grams to about $2.65956 \times^{-7}$ grams of L-arginine, from about $9.62508 \times^{-8}$ grams to about $1.06382 \times^{-7}$ grams of potassium sorbate, from about $6.97818 \times^{-8}$ grams to about $7.71272 \times^{-8}$ grams of sodium nitrite, from about $9.9224 \times^{-9}$ grams to about $1.09669 \times^{-8}$ grams of vitamin A, from about $1.73452 \times^{-10}$ grams to about $1.9171 \times^{-10}$ grams of vitamin B1, from about $1.31008 \times^{-10}$ grams to about $1.44798 \times^{-10}$ grams of vitamin B2, from about $1.67102 \times^{-9}$ grams to about $1.84692 \times^{-9}$ grams of vitamin B3, from about $1.67102 \times^{-9}$ grams to about $1.84692 \times^{-9}$ grams of vitamin B6, from about $5.01306 \times^{-13}$ grams to about $5.54075 \times^{-13}$ grams of vitamin B12, from about $5.01306 \times^{-9}$ grams to about $5.54075 \times^{-9}$ grams of vitamin C, from about $7.93792 \times^{-10}$ grams to about $8.77349 \times^{-10}$ grams of vitamin D3, from about $5.78806 \times^{11}$ grams to about $6.39733 \times^{11}$ grams of vitamin E, from about $1.50392 \times^{11}$ grams to about $1.66223 \times^{11}$ grams of vitamin H, from about $1.60418 \times^{11}$ grams to about $1.77304 \times^{11}$ grams of folic acid, from about $7.35249 \times^{11}$ grams to about $8.12643 \times^{11}$ grams of copper, from about $6.3833 \times^{-10}$ grams to about $7.05522^{-10}$ grams of iron, from about $5.48952 \times^{-12}$ grams to about $6.06736 \times^{-12}$ grams of potassium Iodide, from about $3.34204 \times^{-9}$ grams to about $3.69383 \times^{-9}$ grams of calcium carbonate, and from about $5.38068 \times^{-10}$ grams to about $5.94707 \times^{-10}$ grams of zinc; and wherein the nutraceutical/supplement composition is provided to an individual via an administration route that substantially avoids first pass metabolism.

Additional embodiments are disclosed in the detailed description provided below. While the presently described technology will be provided in connection with one or more preferred embodiments, it will be understood by those skilled in the art that the presently described technology is not limited to those embodiments. To the contrary, the presently described technology includes all alternatives, modifications, and equivalents as may be included within the spirit and scope of the appended claims.

DETAILED DESCRIPTION OF THE INVENTION

Definitions

Figure 1:
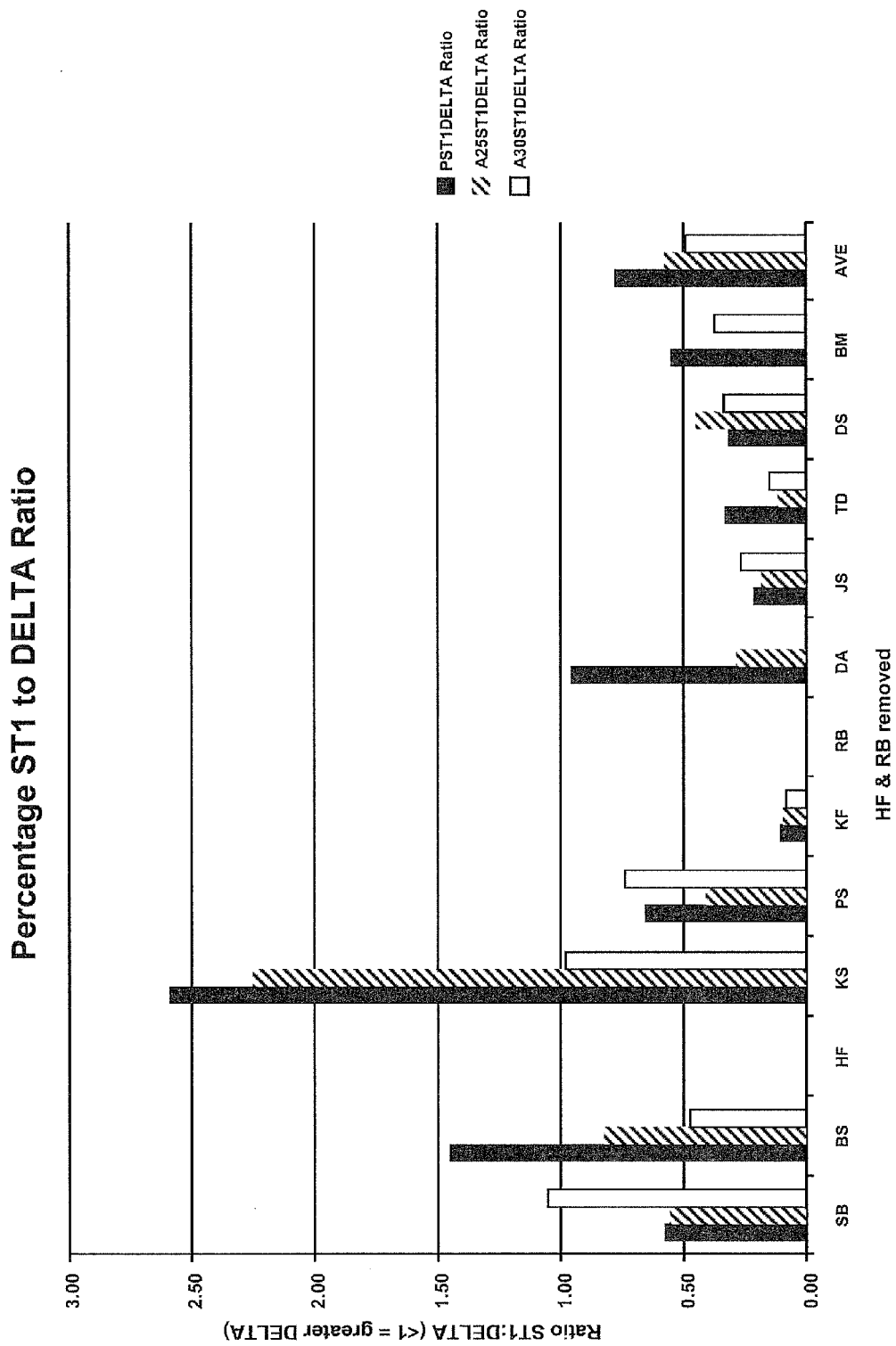
FIG. 1 is a bar graph of the ratio between stage 1 sleep percentage and DELTA sleep percentage for subjects who were administered placebo and the nutraceutical composition presented in Table 1.

"Sleep" is defined generally herein as the body's rest cycle which is triggered by a complex group of hormones that respond to cues from the body itself and the environment. In response to these cues, an individual will begin to fall asleep and, normally, progress through a number of sleep stages (e.g., waking, non-rapid eye movement (e.g., non-REM or NREM) stages 1 to 4, and/or rapid eye movement (e.g., REM) sleep).

For example, sleep can be initiated by entering the "waking" sleep stage. The waking stage is referred to as relaxed wakefulness, because this is the stage in which the body prepares for sleep. All people fall asleep with tense muscles, their eyes moving erratically. Then, as a person becomes sleepier, the body begins to slow down. Muscles begin to relax, and eye roll movement slows.

Next, an individual can begin "non-rapid eye movement sleep" or "NREM sleep". About 80 percent of sleep is dreamless, NREM sleep. During NREM sleep, the breathing and heart rate are slow and regular, the blood pressure is low, and the sleeper is relatively still. NREM sleep is divided into four stages of increasing depth of sleep: Stage 1, Stage 2, and Stages 3 and 4. NREM sleep typically lasts from approximately 90 to 120 minutes, each stage lasting anywhere from 5 to 15 minutes. Stages 2 and 3 repeat backwards before rapid eye movement (REM) sleep is attained. Therefore, a normal sleep cycle has the following pattern: waking, stage 1, 2, 3, 4, 3, 2, REM. Usually, REM sleep occurs approximately 90 minutes after sleep onset.

"Latency" is defined herein as the amount of time required for an individual to enter a sleep stage. "Stage 1 latency" is defined herein as the time in minutes from when an individual begins attempting to fall asleep until the onset of the first bout of Stage 1 sleep. "Stage 2 latency" is defined herein as the time in minutes from sleep onset to the onset of the first bout of Stage 2 sleep. "Stage 3/4 latency" or "DELTA latency" is defined herein as the time in minutes from sleep onset to the onset of the first bout of Stage 3/4 sleep. "REM Latency" is defined herein as the time in minutes from sleep onset to the onset of the first bout of REM sleep.

It is also important to note that sleep stages are not necessarily sequential. For instance, if a person is exhausted he or she may skip Stages 1 and 2 and move directly into Delta or REM. Most adults utilize approximately eight hours of sleep on a regular schedule to function well, although some require less, and others more. Children, particularly teenagers, often need nine or ten hours for optimal functioning.

"Stage 1" sleep, or drowsiness, is often described as first in the sequence, especially in models where waking is not included. Polysomnography (PSG) can show a 50% reduction in activity between wakefulness and stage 1 sleep. The eyes are closed during Stage 1 sleep, but if aroused from it, a person may feel as if he or she has not slept. Stage 1 may last for approximately 5 to 10 minutes.

"Stage 2" sleep is a period of light sleep during which PSG readings can show intermittent peaks and valleys, or positive and negative waves. These waves indicate spontaneous periods of muscle tone mixed with periods of muscle relaxation. Muscle tone of this kind can be seen in other stages of sleep as a reaction to auditory stimuli. The heart rate slows, and body temperature decreases. At this point, the body prepares to enter "deep sleep" stages.

"Stages 3 and 4" or "DELTA" sleep are deep sleep stages. These stages are known as slow-wave sleep. During slow-wave sleep, the electromyogram records can show waves of high amplitude, indicating a pattern of deep sleep and rhythmic continuity.

"Rapid Eye Movement" or "REM" is a normal stage of sleep characterized by the rapid movement of the eyes. Criteria for REM sleep can include, for example, rapid eye movement, low muscle tone and a rapid, low voltage EEG. REM sleep in adult humans typically occupies approximately 20% to 25% of total sleep, about 90 to 120 minutes of a night's sleep. During a normal night of sleep, humans usually experience about four or five periods of REM sleep; they are quite short at the beginning of the night and longer toward the end. During REM, the activity of the brain's neurons is quite similar to that during waking hours; for this reason, the sleep stage may be called paradoxical sleep. This means that there are no dominating brain waves during REM sleep. Vividly recalled dreams mostly occur during REM sleep.

"Sleep Efficiency" is defined herein as a percentage that reflects the percentage of time asleep versus the total time in bed. E.g., total sleep time (TST)=386 minutes; Sleep period total/time in bed=424 minutes; Sleep Efficiency=89.1%.

"Stage specific % of TST" is the percentage of TST of any given stage (accumulated) E.g., TST=386 minutes; total time in REM=48 minutes; REM % TST=12.4%.

The "Percentage of Stage 1 to DELTA" or "Percentage of Stage 1 to REM" is defined herein as a percentage of the time spent in Stage 1 sleep relative to the amount of time spent in DELTA or REM sleep. Since DELTA and REM are restorative sleep stages that are often limited in disordered sleep, a decrease of the amount of Stage 1 sleep relative to DELTA and/or REM sleep is considered beneficial, by at least those familiar with the field of sleep study.

Sleep studies are often performed to access an individuals overall quality of sleep and/or to diagnose any sleep disorders that may be present. The data during a sleep study is analyzed in 30 second windows termed "epochs". The staging of sleep is determined by the predominate features of each epoch. Any interruption in staged sleep greater than 60 seconds (2 epochs) is considered an "awakening".

"Arousals" occur regularly during sleep. Each time one shifts from one stage of sleep to another there is a momentary interruption of sleep or an arousal. If an arousal continues for greater than 60 seconds (2 epochs) it is then generally deemed an awakening.

The "Arousal Index" is defined herein as the total number of Arousals divided by the total number of sleep in hours or total sleep time. E.g., TST=6.43; Total number of arousals=388 Arousal Index=54.9 or 54.9 arousals per hour.

Sleep studies are often used to diagnose and/or confirm suspected sleep disorders such as, but not limited to, "sleep apnea". "Apnea" literally means "without breath." There are three types of apnea: obstructive, central, and mixed. Of the three types of apnea, obstructive is the most common. The root cause of each type of apnea is distinct but, in all three, individuals stop breathing repeatedly during their sleep. This can occur hundreds of times during the night and often for a minute or longer. "Obstructive sleep apnea" or "OSA" is caused by a blockage of the airway, usually when the soft tissue in the rear of the throat collapses and closes during sleep. In "central sleep apnea", the airway is not blocked but the brain fails to signal the muscles to breathe. "Mixed apnea", as the name implies, is a combination of obstructive and central sleep apnea. With each apnea event, the brain briefly arouses people with sleep apnea in order for them to resume breathing, but consequently sleep is extremely fragmented and of poor quality.

The "Apnea Index" is the total number of incidents of Apnea divided by the total number of sleep in minutes or TST. E.g., TST=386; Total number of apneas=50; Apnea Index=7.8 or 7.8 apneas per hour.

Sleep apnea may result in lowered oxygen saturation levels in the blood of affected individuals. "Hypoxic time" is the total time in minutes that the oxygen saturation levels in the blood are below 89.0% E.g., SaO2 of <89:0.0 minutes indicates that the blood oxygen saturation levels did not fall below zero during the duration of sleep analyzed.

"Nap" or "short duration sleep" is typically defined as a short sleep especially during the day. "Short duration sleep" and/or "nap" are defined herein, as a period of sleep lasting one hour or less.

"Polysomnography" or "PSG", also known as a sleep study, is defined herein as a multi-parametric test used in the study of sleep and as a diagnostic tool in sleep medicine. The test result is called a "polysomnogram", also abbreviated "PSG". Polysomnography, as defined herein, is a comprehensive recording of the biophysiological changes that occur during sleep. It is usually performed at night, when most people sleep. The PSG monitors many body functions including brain (EEG), eye movements (EOG), muscle activity or skeletal muscle activation (EMG) and heart rhythm (ECG) during sleep. After the identification of the sleep disorder sleep apnea in the 1970s, the breathing functions respiratory airflow and respiratory effort indicators were added along with peripheral pulse oximetry. Additional details related to performing a PSG and the results of such study are contemplated and included herein as being known to practitioner's having ordinary skill in the sleep study art.

"Enhanced sleep quality" is defined herein as a period of sleep characterized by decreased ratio of stage 1 sleep to DELTA sleep, decreased ratio of stage 1 sleep to REM sleep, decreased number of awakenings, decreased number of arousals, decreased latencies, increased levels of blood oxygen saturation, decreased number of sleep disorder events such as, but not limited to, apneaic events, and/or any other outcome that would be recognized as enhancing sleep quality by one of ordinary skill in the field of sleep studies.

Nutraceutical/Supplement Compositions/Formulations for Enhanced Sleep Quality

It has been unexpectedly and surprisingly discovered that the dose of a vitamin, mineral, or other nutritional ingredient when formulated into one or more compositions of the present technology and adapted for delivery via a system that substantially avoids first pass metabolism, may be significantly reduced while still producing a desired beneficial effect/biological response (e.g., increased sleep duration, decreased latency, etc.). As a result, the ingredients of one or more nutraceutical compositions and/or formulations of the present technology may be provided at substantially lower levels (i.e. ultra-low levels) than conventional amounts (e.g., RDA, UL, UDA, etc.). Furthermore, it has been surprisingly discovered that such ultra-low dosage levels and bioactive delivery systems allow the compositions/formulations of the present technology to be repeatedly and flexibly administered to an animal or human for the enhancement and augmentation of those biological functions (e.g., stages of sleep) known to be influenced by any of the individual components.

Without wanting to be bound by any particular theory, it is believed that administration of the ultra-low dose nutraceuticals of the present technology results in the initiation of signaling pathways (negative and/or positive feedback regulatory processes) and/or cascades that induce desired biological responses including, but not limited to, enhanced sleep quality.

For example, it is believed that due to the ultra-low dosage levels utilized in the present technology, a specific composition may be taken by an individual multiple times within each dosing period (e.g., within each 24 hour, 6 hour, or 1 hour period). Alternatively, an individual may take multiple, different compositions or formulations of the present technology within a dosing period to generate varied biological responses or effects, namely those associated with sleep disorders or the different stages of sleep. Thus, the presently described technology may be utilized in a system which allows an individual to biologically configure their dietary supplement intake throughout a dosing period or multiple dosing periods, based on their individual sleep needs or disorder(s).

Accordingly, the presently described technology provides for one or more ultra-low dose nutraceutical compositions or formulations comprising vitamins, minerals, enzymes, amino acids, adjuncts, and additives that can be administered to enhance sleep quality or treat sleep disorders.

Below is a detailed description of some of the components in the presently described ultra-low dose nutraceutical formulations/compositions of the present technology, their delivery systems for administration, and the sleep-based biological effects elicited thereby.

Water

The water can vary from source to source, but preferably contains at least calcium and magnesium in the amounts disclosed herein (below). Most preferably, the presently described technology utilizes water from an Appalachia water source, preferably a water source from the Eastern slope of the Shenandoah Valley. Different water sources would require empirical analysis of its constituents to ensure that the dosage amounts are consistent with spirit of the presently described technology.

The water is preferably filtered to purify and refine it from the certain, selected water-source. The filter is preferably a commercially available filter having a pore size of about 0.1 micron. An example of components that the water can include, and tolerances for the amounts of those components, is set forth below:

Calcium 0 mg/L to about 12.4 mg/L (+) 25%
Chromium 0 mg/L to about 0.001 mg/L (+) 25%
Magnesium 0 mg/L to about 5.8 mg/L (+) 25%
Manganese 0 mg/L to about 0.001 mg/L (+) 25%
Potassium 0 mg/L to about 1.4 mg/L (+) 25%
Sodium 0 mg/L to about 1.6 mg/L (+) 25%

In an additional embodiment, the water may contain from 0 to 0.10 milligrams/Liter (+) 25% of at least one nitrate and from 0 to 0.10 milligrams/Liter (+) 25% of at least one nitrite.

Any of these preferred components of the water may range from 0 to about (+) 25%. The pH of the water can range from about 5 to about 7.5. Preferably, the pH of the water is about 7.50 at 25 degrees Celsius.

In at least one embodiment, a nutraceutical composition of the present technology contains water in the volume of from about 0.15 milliliters to about 0.4 milliliters.

Vitamins, Minerals, Enzymes, and Amino Acids

The compositions of the present technology can include any of the water-soluble and/or fat-soluble vitamins, a coenzyme such as $Q_{10}$, essential and/or non-essential amino acids (including standard and non-standard amino acids), and minerals including without limitation calcium, phosphorus, magnesium, sodium, potassium, chloride, chromium, copper, fluoride, iodine, iron, manganese, molybdenum, selenium and zinc. The presently described technology can also include other ingredients, for example, nitrate, nitrite, folic acid, additives, and adjuncts such as, but not limited to, caffeine. In addition, certain embodiments of the presently described ultra-low dose nutraceutical are substantially free of chloride compounds other than magnesium chloride.

The one or more components of the ultra-low dose nutraceutical compositions or formulations of the present invention can comprise at least five of the following ingredients or components: magnesium chloride, potassium carbonate, calcium ascorbate, ascorbic acid, caffeine, niacin, potassium benzoate, chromium picolinate, chromium polynicotinate, coenzyme Q10, L-glutamine, potassium sorbate, calcium ascorbate, sodium nitrite, L-arginine, sodium ascorbate, copper, iron, potassium iodide, calcium carbonate, zinc, ascorbic acid, niacin, vitamin A, vitamin B1, vitamin B2, vitamin B3, vitamin B6, vitamin B12, vitamin C, vitamin D3, vitamin E, vitamin H, folic acid, and combinations and derivatives thereof. Illustrative examples of ultra-low dose nutraceutical base mixtures and pre-mixes of the present invention are presented in U.S. patent application Ser. No. 11/483,208, which is hereby incorporated by reference in its entirety.

At least one embodiment of the present invention contains magnesium chloride, sodium ascorbate, potassium carbonate, calcium ascorbate, potassium sorbate, sodium nitrite, potassium benzoate, chromium picolinate, chromium polynicotinate, copper, iron, potassium iodide, calcium carbonate, zinc, ascorbic acid, niacin, vitamin A, vitamin B1, vitamin B2, vitamin B3, vitamin B6, vitamin B12, vitamin C, vitamin D3, vitamin E, vitamin H, folic acid, caffeine, L-glutamine, L-arginine, coenzyme Q10, and combinations and derivatives thereof.

In another embodiment, the nutraceutical/supplement composition/formulation of the present technology contains from about $1.25 \times 10^{-13}$ grams to about $3.5 \times 10^{-3}$ grams of at least one mineral, from about $6 \times 10^{-9}$ grams to about $6 \times 10^{-6}$ grams of at least one enzyme, from about $2 \times 10^{-14}$ grams to about $1.8 \times 10^{-4}$ grams of at least one vitamin, from about $3 \times 10^{-8}$ grams to about $3 \times 10^{-4}$ grams of at least one adjunct, and from about $1.5 \times 10^{-8}$ grams to about $1.5 \times 10^{-2}$ grams of at least one amino acid; and each compound/component can be, for example, in additional multiplied factors thereof, (e.g. ×0.0001, ×0.001, ×0.01, ×0.01, ×1, ×2, ×2.5, ×5, ×10, ×100, etc).

Adjuncts and Additives

The compositions of the present technology may also include additives such as, but not limited to, the components described herein.

Film Forming Agents

Film forming agents include, but are not limited to, cellulose polymers, polyethylene oxide, pullulan, hydroxypropylmethyl cellulose, hydroxypropyl cellulose, polyvinyl pyrrolidone, polyvinyl alcohol, sodium alginate, polyethylene glycol, xanthan gum, tragacanth gum, guar gum, acacia gum, Arabic gum, polyacrylic acid, amylase, starch, dextrin, pectin, chitin, chitosin, levan, elsinan, collagen, gelatin, zein, gluten, soy protein isolate, whey protein isolate, casein, and mixtures thereof.

The polymer may be water soluble, water swellable, water insoluble or a combination of one or more either water soluble, water swellable or water insoluble polymers. The polymer may include cellulose or a cellulose derivative. Specific examples of useful water soluble polymers include, but are not limited to, polyethylene oxide (PEO), pullulan, hydroxypropylmethyl cellulose (HPMC), hydroxyethyl cellulose (HPC), hydroxypropyl cellulose, polyvinyl pyrrolidone, carboxymethyl cellulose, polyvinyl alcohol, sodium aginate, polyethylene glycol, xanthan gum, tragancanth gum, guar gum, acacia gum, arabic gum, polyacrylic acid, methylmethacrylate copolymer, carboxyvinyl copolymers, starch, gelatin, and combinations thereof. Specific examples of useful water insoluble polymers include, but are not limited to, ethyl cellulose, hydroxypropyl ethyl cellulose, cellulose acetate phthalate, hydroxypropyl methyl cellulose phthalate and combinations thereof.

As used herein the phrase "water soluble polymer" and variants thereof refer to a polymer that is at least partially soluble in water, and desirably fully or predominantly soluble in water, or absorbs water. Polymers that absorb water are often referred to as being water swellable polymers. The materials useful with the present invention may be water soluble or water swellable at room temperature and other temperatures, such as temperatures exceeding room temperature. Moreover, the materials may be water soluble or water swellable at pressures less than atmospheric pressure. Desirably, the water soluble polymers are water soluble or water swellable having at least about 20 percent by weight water uptake. Water swellable polymers having about 25 or greater percent by weight water uptake are also useful. Films or dosage forms of the present invention formed from such water soluble polymers are desirably sufficiently water soluble to be dissolvable upon contact with bodily fluids.

Other polymers useful for incorporation into the films of the present invention include biodegradable polymers, copolymers, block polymers and combinations thereof. Among the known useful polymers or polymer classes which meet the above criteria are: poly(glycolic acid) (PGA), poly(lactic acid) (PLA), polydioxanoes, polyoxalates, poly(α-esters), polyanhydrides, polyacetates, polycaprolactones, poly(orthoesters), polyamino acids, polyaminocarbonates, polyurethanes, polycarbonates, polyamides, poly(alkyl cyanoacrylates), and mixtures and copolymers thereof. Additional useful polymers include, stereopolymers of L- and D-lactic acid, copolymers of bis(p-carboxyphenoxy)propane acid and sebacic acid, sebacic acid copolymers, copolymers of caprolactone, poly(lactic acid)/poly(glycolic acid)/polyethyleneglycol copolymers, copolymers of polyurethane and (poly(lactic acid), copolymers of polyurethane and poly (lactic acid), copolymers of α-amino acids, copolymers of α-amino acids and caproic acid, copolymers of α-benzyl glutamate and polyethylene glycol, copolymers of succinate and poly(glycols), polyphosphazene, polyhydroxy-alkanoates and mixtures thereof. Binary and ternary systems are contemplated.

Other specific polymers useful include those marketed under the Medisorb and Biodel trademarks. The Medisorb materials are marketed by the Dupont Company of Wilmington, Del. and are generically identified as a "lactide/glycolide co-polymer" containing "propanoic acid, 2-hydroxy-polymer with hydroxy-polymer with hydroxyacetic acid." Four such polymers include lactide/glycolide 100 L, believed to be 100% lactide having a melting point within the range of about 338° to about 347° F. (about 170° to about 175° C.); lactide/glycolide 100 L, believed to be 100% glycolide having a melting point within the range of about 437° to about 455° F. (about 225° to about 235° C.); lactide/glycolide 85/15, believed to be approximately 85% lactide and approximately 15% glycolide with a melting point within the range of about 338° to about 347° F. (about 170° to about 175° C.); and lactide/glycolide 50/50, believed to be a copolymer of about 50% lactide and about 50% glycolide with a melting point within the range of about 338° to about 347° F. (about 170° to about 175° C.). The Biodel materials represent a family of various polyanhydrides which differ chemically.

Although a variety of different polymers may be used, it is desired to select polymers to provide a desired viscosity of the mixture prior to drying. For example, if the active or other components are not soluble in the selected solvent, a polymer that will provide a greater viscosity is desired to assist in maintaining uniformity. On the other hand, if the components are soluble in the solvent, a polymer that provides a lower viscosity may be preferred.

The polymer plays an important role in affecting the viscosity of the film. Viscosity is one property of a liquid that controls the stability of the active in an emulsion, a colloid or a suspension. Generally the viscosity of the matrix will vary from about 400 cps to about 100,000 cps, preferably from about 800 cps to about 60,000 cps, and most preferably from about 1,000 cps to about 40,000 cps. Desirably, the viscosity of the film-forming matrix will rapidly increase upon initiation of the drying process.

The viscosity may be adjusted based on the selected active depending on the other components within the matrix. For example, if the component is not soluble within the selected solvent, a proper viscosity may be selected to prevent the component from settling which would adversely affect the uniformity of the resulting film. The viscosity may be adjusted in different ways. To increase viscosity of the film matrix, the polymer may be chosen of a higher molecular weight or crosslinkers may be added, such as salts of calcium, sodium and potassium. The viscosity may also be adjusted by adjusting the temperature or by adding a viscosity increasing component. Components that will increase the viscosity or stabilize the emulsion/suspension include higher molecular weight polymers and polysaccharides and gums, which include without limitation, alginate, carrageenan, hydroxypropyl methyl cellulose, locust bean gum, guar gum, xanthan gum, dextran, gum arabic, gellan gum and combinations thereof.

It has also been observed that certain polymers which when used alone would ordinarily require a plasticizer to achieve a flexible film, can be combined without a plasticizer and yet achieve flexible films. For example, HPMC and HPC when used in combination provide a flexible, strong film with the appropriate plasticity and elasticity for manufacturing and storage. No additional plasticizer or polyalcohol is needed for flexibility.

Flavors

Flavors may be chosen from natural and synthetic flavoring liquids. An illustrative list of such agents includes volatile oils, synthetic flavor oils, flavoring aromatics, oils, liquids, oleoresins or extracts derived from plants, leaves, flowers, fruits, stems and combinations thereof. A non-limiting representative list of examples includes mint oils, cocoa, and citrus oils such as lemon, orange, grape, lime and grapefruit and fruit essences including apple, pear, peach, grape, strawberry, raspberry, cherry, plum, pineapple, apricot or other fruit flavors.

Useful flavors or flavoring agents include natural and artificial flavors. These flavorings may be chosen from synthetic flavor oils and flavoring aromatics, and/or oils, oleo resins and extracts derived from plants, leaves, flowers, fruits and so forth, and combinations thereof. Non-limiting flavor oils include: spearmint oil, cinnamon oil, peppermint oil, clove oil, bay oil, thyme oil, cedar leaf oil, oil of nutmeg, oil of sage, and oil of bitter almonds. Also useful are artificial, natural or synthetic fruit flavors such as vanilla, chocolate, coffee, cocoa and citrus oil, including lemon, orange, grape, lime and grapefruit, and fruit essences including apple, pear, peach, strawberry, raspberry, cherry, plum, pineapple, apricot and the like. These flavorings can be used individually or in combination. Commonly used flavors include mints such as peppermint, artificial vanilla, cinnamon derivatives, and various fruit flavors, whether employed individually or in combination. Flavorings such as aldehydes and esters including cinnamylacetate, cinnamaldehyde, citral, diethylacetal, dihydrocarvyl acetate, eugenyl formate, p-methylanisole, and the like may also be used. Further examples of aldehyde flavorings include, but are not limited to acetaldehyde (apple); benzaldehyde (cherry, almond); cinnamicaldehyde (cinnamon); citral, i.e., alpha citral (lemon, lime); neral, i.e. beta citral (lemon, lime); decanal (orange, lemon); ethyl vanillin (vanilla, cream); heliotropine, i.e., piperonal (vanilla, cream); vanillin (vanilla, cream); alpha-amyl cinnamaldehyde (spicy fruity flavors); butyraldehyde (butter, cheese); valeraldehyde (butter, cheese); citronellal (modifies, many types); decanal (citrus fruits); aldehyde C-8 (citrus fruits); aldehyde C-9 (citrus fruits); aldehyde C-12 (citrus fruits); 2-ethyl butyraldehyde (berry fruits); hexenal, i.e. trans-2 (berry fruits); tolyl aldehyde (cherry, almond); veratraldehyde (vanilla); 12,6-dimethyl-5-heptenal, i.e. melonal (melon); 2 dimethyloctanal (greenfruit); and 2-dodecenal (citrus, mandarin); cherry; grape; mixtures thereof; and the like.

Other useful flavorings include aldehydes and esters such as benzaldehyde (cherry, almond), citral i.e., alphacitral (lemon, lime), neral, i.e., beta-citral (lemon, lime), decanal (orange, lemon), aldehyde C-8 (citrus fruits), aldehyde C-9 (citrus fruits), aldehyde C-12 (citrus fruits), tolyl aldehyde (cherry, almond), 2,6-dimethyloctanol (green fruit), and 2-dodecenal (citrus, mandarin), combinations thereof and the like.

The amount of flavoring employed is normally a matter of preference, subject to such factors as flavor type, individual flavor, and strength desired. The amount may be varied in order to obtain the result desired in the final product. Such variations are within the capabilities of those skilled in the art without the need for undue experimentation. In general, amounts of about 0.1 to about 30 weight (wt) % are useful with the practice of the present invention.

Sweeteners

Suitable sweeteners include both natural and artificial sweeteners. Non-limiting examples of suitable sweeteners include, e.g. water-soluble sweetening agents such as monosaccharides, disaccharides and polysaccharides such as xylose, ribose, glucose (dextrose), mannose, galactose, fructose (levulose), sucrose (sugar), high fructose corn syrup, maltose, invert sugar (a mixture of fructose and glucose derived from sucrose), partially hydrolyzed starch, corn syrup solids, and dihydrochalcones; water-soluble artificial sweeteners such as the soluble saccharin salts, i.e., sodium or calcium saccharin salts, cyclamate salts, the sodium, ammonium or calcium salt of 3,4-dihydro-6-methyl-1,2,3-oxathiazine-4-one-2,2-dioxide, the potassium salt of 3,4-dihydro-6-methyl-1,2,3-oxathiazine-4-one-2,2-dioxide (acesulfame-K), the free acid form of saccharin and the like; dipeptide based sweeteners, such as L-aspartic acid derived sweeteners, such as L-aspartyl-L-phenylalanine methyl ester (aspartame), L-alpha-aspartyl-N-(2,2,4,4-tetramethyl-3-thietanyl)-D-alaninamide hydrate, methyl esters of L-aspartyl-L-phenylglycerin and L-aspartyl-L-2,5,dihydrophenylglycine, L-aspartyl-2,5-dihydro-L-phenylalanine, L-aspartyl-L-(1-cyclohexyen)-alanine, and the like; water-soluble sweeteners derived from naturally occurring water-soluble sweeteners, such as a chlorinated derivatives of ordinary sugar (sucrose), known, for example, as sucralose; protein based sweeteners such as thaurnatoccous danielli (Thaurnatin I and II); and naturally occurring high intensity sweeteners, such as Lo Han Kuo, stevia, steviosides, monellin, and glycyrrhizin.

In general, an effective amount of auxiliary sweetener is utilized to provide the level of sweetness desired for a particular composition, and this amount will vary with the sweetener selected. This amount will normally be about 0.01% to about 10% by weight of the composition. These amounts may be used to achieve a desired level of sweetness independent from the flavor level achieved from any optional flavor oils used. Of course, sweeteners need not be added to films intended for non-oral administration.

Colors

Color additives useful in this invention include food, drug and cosmetic colors (FD&C), drug and cosmetic colors (D&C), or external drug and cosmetic colors (Ext. D&C). These colors are dyes, their corresponding lakes, and certain natural and derived colorants. Lakes are dyes absorbed on aluminum hydroxide.

Other examples of coloring agents include known azo dyes, organic or inorganic pigments, or coloring agents of natural origin. Inorganic pigments are preferred, such as the oxides or iron or titanium, these oxides, being added in concentrations ranging from about 0.001 to about 10%, and preferably about 0.5 to about 3%, based on the weight of all the components.

Other Additives

A variety of other additives and fillers may also be added to the films of the present invention. These may include, without limitation, surfactants; plasticizers which assist in compatibilizing the components within the mixture; polyalcohols; anti-foaming agents, such as silicone-containing compounds, which promote a smoother film surface by releasing oxygen from the film; thermo-setting gels such as pectin, carageenan, and gelatin, which help in maintaining the dispersion of components; and inclusion compounds, such as cyclodextrins and caged molecules, which improve the solubility and/or stability of certain active components.

The variety of additives that can be incorporated into the compositions of the present technology can provide a variety of different functions. Examples of classes of additives include excipients, lubricants, buffering agents, stabilizers, blowing agents, pigments, coloring agents, fillers, bulking agents, sweetening agents, flavoring agents, fragrances, release modifiers, adjuvants, plasticizers, flow accelerators, mold release agents, polyols, granulating agents, diluents, binders, buffers, absorbents, glidants, adhesives, anti-adherents, acidulants, softeners, resins, demulcents, solvents, surfactants, emulsifiers, elastomers and mixtures thereof. These additives may be added with the active ingredient(s).

Useful additives include, for example, gelatin, vegetable proteins such as sunflower protein, soybean proteins, cotton seed proteins, peanut proteins, grape seed proteins, whey proteins, whey protein isolates, blood proteins, egg proteins, acrylated proteins, water-soluble polysaccharides such as alginates, carrageenans, guar gum, agar-agar, xanthan gum, gellan gum, gum arabic and related gums (gum ghatti, gum karaya, gum tragancanth), pectin, water-soluble derivatives of cellulose: alkylcelluloses hydroxyalkylcelluloses and hydroxyalkylalkylcelluloses, such as methylcellulose, hydroxymethylcellulose, hydroxyethylcellulose, hydroxypropylcellulose, hydroxyethylmethylcellulose, hydroxypropylmethylcellulose, hydroxybutylmethylcellulose, cellulose esters and hydroxyalkylcellulose esters such as cellulose acetate phthalate (CAP), hydroxypropylmethylcellulose (HPMC); carboxyalkylcelluloses, carboxyalkylalkylcelluloses, carboxyalkylcellulose esters such as carboxymethylcellulose and their alkali metal salts; water-soluble synthetic polymers such as polyacrylic acids and polyacrylic acid esters, polymethacrylic acids and polymethacrylic acid esters, polyvinylacetates, polyvinylalcohols, polyvinylacetatephthalates (PVAP), polyvinylpyrrolidone (PVP), PVY/vinyl acetate copolymer, and polycrotonic acids; also suitable are phthalated gelatin, gelatin succinate, crosslinked gelatin, shellac, water soluble chemical derivatives of starch, cationically modified acrylates and methacrylates possessing, for example, a tertiary or quaternary amino group, such as the diethylaminoethyl group, which may be quaternized if desired; and other similar polymers.

Such extenders may optionally be added in any desired amount desirably within the range of up to about 80%, desirably about 3% to 50% and more desirably within the range of 3% to 20% based on the weight of all components.

Further additives may be inorganic fillers, such as the oxides of magnesium aluminum, silicon, titanium, etc. desirably in a concentration range of about 0.02% to about 3% by weight and desirably about 0.02% to about 1% based on the weight of all components.

Binders may be selected from a wide range of materials such as hydroxypropylmethylcellulose, ethylcellulose, or other suitable cellulose derivatives, povidone, acrylic and methacrylic acid co-polymers, pharmaceutical glaze, gums, milk derivatives, such as whey, starches, and derivatives, as well as other conventional binders known to persons skilled in the art. Exemplary non-limiting solvents are water, ethanol, isopropyl alcohol, methylene chloride or mixtures and combinations thereof. Exemplary non-limiting bulking substances include sugar, lactose, gelatin, starch, and silicon dioxide.

Further examples of additives are plasticizers which include polyalkylene oxides, such as polyethylene glycols, polypropylene glycols, polyethylene-propylene glycols, organic plasticizers with low molecular weights, such as glycerol, glycerol monoacetate, diacetate or triacetate, triacetin, polysorbate, cetyl alcohol, propylene glycol, sorbitol, sodium diethylsulfosuccinate, triethyl citrate, tributyl citrate, and the like, added in concentrations ranging from about 0.5% to about 30%, and desirably ranging from about 0.5% to about 20% based on the weight of the polymer. Preferred plasticizers may be selected from the group consisting of diethyl phthalate, diethyl sebacate, triethyl citrate, cronotic acid, propylene glycol, butyl phthalate, dibutyl sebacate, castor oil and mixtures thereof, without limitation. As is evident, the plasticizers may be hydrophobic as well as hydrophilic in nature. Water-insoluble hydrophobic substances, such as diethyl phthalate, diethyl sebacate and castor oil are used to delay the release of water-soluble vitamins, such as vitamin B6 and vitamin C. In contrast, hydrophilic plasticizers are used when water-insoluble vitamins are employed which aid in dissolving the encapsulated film, making channels in the surface, which aid in nutritional composition release.

Additional compounds can be added to improve the flow properties of the starch material such as animal or vegetable fats, desirably in their hydrogenated form, especially those which are solid at room temperature. These fats desirably have a melting point of 50° C. or higher. Preferred are tri-glycerides with C12-, C14-, C16-, C18-, C20- and C22-fatty acids. These fats can be added alone without adding extenders or plasticizers and can be advantageously added alone or together with mono- and/or di-glycerides or phosphatides, especially lecithin. The mono- and di-glycerides are desirably derived from the types of fats described above, i.e. with C12-, C14-, C16-, C18-, C20- and C22-fatty acids.

The total amounts used of the fats, mono-, di-glycerides and/or lecithins are up to about 5% and preferably within the range of about 0.5% to about 2% by weight of the total composition.

It should be understood that in addition to the ingredients particularly mentioned above, the formulations of the present technology can include other suitable agents such as preservatives and antioxidants. Such antioxidants would be food acceptable and could include, for example, vitamin E, carotene, BHT or other antioxidants known to those of skill in the art.

Anti-Foaming and De-Foaming Compositions

Anti-foaming and/or de-foaming components may also be used with the films of the present invention. These components aid in the removal of air, such as entrapped air, from the film-forming compositions. As described above, such entrapped air may lead to non-uniform films. Simethicone is one particularly useful anti-foaming and/or de-foaming agent. The present invention, however, is not so limited and other anti-foam and/or de-foaming agents may suitable be used.

As a related matter, simethicone and related agents may be employed for densification purposes. More specifically, such agents may facilitate the removal of voids, air, moisture, and similar undesired components, thereby providing denser and thus more uniform films. Agents or components which perform this function can be referred to as densification or densifying agents. As described above, entrapped air or undesired components may lead to non-uniform films.

Simethicone is generally used in the medical field as a treatment for gas or colic in babies. Simethicone is a mixture of fully methylated linear siloxane polymers containing repeating units of polydimethylsiloxane which is stabilized with trimethylsiloxy end-blocking unites, and silicon dioxide. It usually contains 90.5-99% polymethylsiloxane and 4-7% silicon dioxide. The mixture is a gray, translucent, viscous fluid which is insoluble in water.

In order to prevent the formation of air bubbles in the films of the present invention, the mixing step can be performed under vacuum. However, as soon as the mixing step is completed, and the film solution is returned to the normal atmosphere condition, air will be re-introduced into or contacted with the mixture. In many cases, tiny air bubbles will be again trapped inside this polymeric viscous solution. The incorporation of simethicone into the film-forming composition either substantially reduces or eliminates the formation of air bubbles.

Simethicone may be added to the film-forming mixture as an anti-foaming agent in an amount from about 0.01 weight percent to about 5.0 weight percent, more desirably from about 0.05 weight percent to about 2.5 weight percent, and most desirably from about 0.1 weight percent to about 1.0 weight percent.

Delivery System(s)

For the present technology, any dosage form can be utilized. Those dosage forms can include, for example, an oral film, tablet, pill, liquid, sublingual liquid, capsule, lozenge, troche, suppository, transdermal patch, nasal sprays, dragus, slurry, suspension, or emulsion. For this particular technology, dosage administration routes are preferably those that by-pass first pass metabolism such as sublingual, buccal, nasal, transdermal, intradermal, intramuscular, intravenous and certain rectal routes. Again, without being bound by any particular theory this is due to the present technology being believed to have enhanced efficacy by circumventing dosage administration routes which would undergo first pass metabolism (gastrointestinal, in particular).

Compositions of the present technology can be preferably formulated for parenteral absorption. Parenteral absorption generally comprises absorption by way other than the gastrointestinal track and without significant first pass metabolism. By way of example and without limitation, parenteral absorption can be pre-gastric, topical, optical, intravenous, and/or by oral or nasal inhalation. Pre-gastric absorption as used herein comprises absorption of an ingredient, composition, or formulation of the present technology from that part of the alimentary canal prior to the stomach, and includes without limitation buccal, sublingual, oropharyngeal and esophageal absorption. It is envisaged that such pre-gastric absorption will occur primarily across the mucous membranes in the mouth, pharynx and esophagus. The oral mucosa has a thin epithelium and a rich vascularity that favors absorption. Blood capillaries are extremely close to the surface in these areas and readily absorb the ingredients into the blood stream. The flow is from this area of the mouth to the Carotid Artery and it is envisaged that distribution to the brain and the rest of the body will be rapid, thereby resulting in greatly enhanced efficacy and/or rates of response. The present technology, however, is not limited to any one method of delivery, and envisions delivery via any tissue with an adequate rate of absorption, which avoids first pass metabolism.

It is further believed that ingredients absorbed by pre-gastric absorption will pass substantially into the systemic circulatory system and thereby avoid the gastrointestinal track and first pass metabolism in the liver. Accordingly, bioavailability of one or more active ingredients, additives, adjuncts and the like of the present technology delivered in this way may also be increased. Additionally, the bioavailability of a number of vitamins, minerals, amino acids, co-enzymes, and/or other nutrients in concert can also be increased. It is desired and in some embodiments preferred that the dose of an ingredient/component may be minimized, while still producing the desired beneficial effects, with close to zero order kinetics (immediate efficacy) thereby decreasing the required dose. These concentrations may vary and will be selected primarily on the desired biological response and dosage form selected, especially those related directly or indirectly to or for sleep and/or sleep disorders.

U.S. Pat. Nos. 6,596,298; 6,569,463; 5,948,430; 6,592,887; 5,629,003; 6,419,903; and 6,316,029 disclose various delivery systems which may be utilized in the practice of the present technology.

One particularly preferred method of delivery, although the present technology is not limited to any one method, is a sublingual liquid provided in a volume of from about 0.15 milliliters to about 0.4 milliliters. Additional information regarding the dosage forms and levels of the presently described technology are presented in U.S. patent application Ser. No. 11/483,208, which is hereby incorporated by reference in its entirety.

Biological Responses/Sleep/Sleep Disorders

In one or more embodiments of the present technology, the particular biological response is enhanced sleep quality. "Enhanced sleep quality" is defined herein as a period of sleep characterized by decreased ratio of stage 1 sleep to DELTA sleep, decreased ratio of stage 1 sleep to REM sleep, decreased number of awakenings, decreased number of arousals, decreased latencies, decreased number of sleep disorder events such as, but not limited to, apneaic events, and/or any other outcomes that would be recognized as enhancing sleep quality by one of ordinary skill in the field of sleep studies. In another embodiment of the present technology, the nutraceutical composition/formulation is used to treat a sleep disorder including, but not limited to, sleep apnea.

Specifically, sublingual administration of the nutraceutical composition/formulation presented in Table 1 produced potentially clinically significant results on a range of sleep dysfunctions including: a shift in percentage time spent in REM and DELTA sleep vs. Stage 1 sleep, a reduction in sleep apnea events for those with clinical sleep apnea, reductions in awakenings and arousals, and reductions in sleep latencies.

TABLE 1

Sleep Enhancing Nutraceutical Composition/Formulation 1

| Ingredient | Grams Per 0.25 milliliter Dose |
|---|---|
| Magnesium Chloride | ≈0.0000005445343474 |
| Sodium Ascorbate | ≈0.0000008168015210 |
| Potassium Carbonate | ≈0.0000008168015210 |
| Calcium Ascorbate | ≈0.0000005445343474 |
| Ascorbic Acid (ester C) | ≈0.0000045377862280 |
| Caffeine | ≈0.0000008621793833 |
| Niacin | ≈0.0000000907557246 |
| Potassium Benzoate | ≈0.0000004084007605 |
| Chromium Picolinate | ≈0.0000000016971320 |
| Chromium Polynicotinate | ≈0.0000000016971320 |
| Coenzyme Q10 | ≈0.0000005672232785 |
| L-Glutamine | ≈0.0000022688931140 |
| L-Arginine | ≈0.0000022688931140 |
| Potassium Sorbate | ≈0.0000009075572456 |
| Sodium Nitrite | ≈0.0000006579790031 |
| Vitamin A | ≈0.0000000935591919 |
| Vitamin B1 | ≈0.0000000016354938 |
| Vitamin B2 | ≈0.0000000012352863 |
| Vitamin B3 | ≈0.0000000157562022 |
| Vitamin B6 | ≈0.0000000157562024 |
| Vitamin B12 | ≈0.0000000000047269 |
| Vitamin C | ≈0.0000000472686065 |
| Vitamin D3 | ≈0.0000000074847354 |
| Vitamin E | ≈0.0000000005457620 |
| Vitamin H | ≈0.0000000001418058 |
| Folic Acid | ≈0.0000000001512595 |
| Copper | ≈0.0000000006932729 |
| Iron | ≈0.0000000060188692 |
| Potassium Iodide | ≈0.0000000000517612 |
| Calcium Carbonate | ≈0.0000000315124044 |
| Zinc | ≈0.0000000050734971 |

In another embodiment of the present technology, enhanced sleep quality may be induced by administration of the nutraceutical formulation/composition presented in Table 2.

TABLE 2

Sleep Enhancing Nutraceutical Composition/Formulation 2

| Ingredient | Grams Per 0.25 milliliter Dose |
|---|---|
| Magnesium Chloride | ≈0.00000009113935634761800 |
| Sodium Ascorbate | ≈0.00000013670903452142700 |
| Potassium Carbonate | ≈0.00000013670903452142700 |
| Calcium Ascorbate | ≈0.00000009113935634761800 |
| Ascorbic Acid (ester C) | ≈0.00000075949463623015000 |
| Caffeine | ≈0.00000014430398088372900 |
| Niacin | ≈0.00000001518989272460300 |
| Potassium Benzoate | ≈0.00000006835451726071350 |
| Chromium Picolinate | ≈0.00000000028405099395008 |
| Chromium Polynicolinate | ≈0.00000000028405099395008 |
| Coenzyme Q10 | ≈0.00000009493682952876870 |
| L-Glutamine | ≈0.00000037974731811507500 |
| L-Arginine | ≈0.00000037974731811507500 |
| Potassium Sorbate | ≈0.00000015189892724603000 |
| Sodium Nitrite | ≈0.00000011012672225337200 |
| Vitamin A | ≈0.00000001565911235820290 |
| Vitamin B1 | ≈0.00000000027373452514128 |
| Vitamin B2 | ≈0.00000000020675131764043 |
| Vitamin B3 | ≈0.00000000263713415357691 |
| Vitamin B6 | ≈0.00000000263713418292936 |
| Vitamin B12 | ≈0.00000000000079114024607 |
| Vitamin C | ≈0.00000000791140246073075 |
| Vitamin D3 | ≈0.00000000125272898863073 |
| Vitamin E | ≈0.00000000009134482208766 |
| Vitamin H | ≈0.00000000002373420738219 |

TABLE 2-continued

Sleep Enhancing Nutraceutical Composition/Formulation 2

| Ingredient | Grams Per 0.25 milliliter Dose |
|---|---|
| Folic Acid | ≈0.0000000000253164878721400 |
| Copper | ≈0.0000000001160339027570900 |
| Iron | ≈0.0000000010073852466662300 |
| Potassium Iodide | ≈0.0000000000008663329668300 |
| Calcium Carbonate | ≈0.0000000005274268307153090 |
| Zinc | ≈0.0000000000849157197393060 |

In an additional embodiment of the present technology, the particular biological response is a short duration sleep, or nap, that is induced by administration of the nutraceutical formulation/composition presented in Table 3.

TABLE 3

Nap/Short Duration Sleep Enhancing Nutraceutical 1

| Ingredient | Grams Per 0.25 milliliter Dose |
|---|---|
| Magnesium Chloride | ≈0.0000003614166022 |
| Sodium Ascorbate | ≈0.0000005421249033 |
| Potassium Carbonate | ≈0.0000005421249033 |
| Calcium Ascorbate | ≈0.0000003614166022 |
| Ascorbic Acid (ester C) | ≈0.0000030118050186 |
| Caffeine | ≈0.0000005722429535 |
| Niacin | ≈0.0000000602361004 |
| Potassium Benzoate | ≈0.0000002710624517 |
| Chromium Picolinate | ≈0.0000000011264151 |
| Chromium Polynicotinate | ≈0.0000000011264151 |
| Coenzyme Q10 | ≈0.0000003764756273 |
| L-Glutamine | ≈0.0000015059025093 |
| L-Arginine | ≈0.0000015059025093 |
| Potassium Sorbate | ≈0.0000006023610037 |
| Sodium Nitrite | ≈0.0000004367117277 |
| Vitamin A | ≈0.0000000620968088 |
| Vitamin B1 | ≈0.0000000010855047 |
| Vitamin B2 | ≈0.0000000008198803 |
| Vitamin B3 | ≈0.0000000104576563 |
| Vitamin B6 | ≈0.0000000104576564 |
| Vitamin B12 | ≈0.0000000000031373 |
| Vitamin C | ≈0.0000000313729689 |
| Vitamin D3 | ≈0.0000000049677447 |
| Vitamin E | ≈0.0000000003622314 |
| Vitamin H | ≈0.0000000000941189 |
| Folic Acid | ≈0.0000000001003935 |
| Copper | ≈0.0000000004601369 |
| Iron | ≈0.0000000039948247 |
| Potassium Iodide | ≈0.0000000000343548 |
| Calcium Carbonate | ≈0.0000000209153126 |
| Zinc | ≈0.0000000033673653 |

In a further embodiment of the present technology, the short duration sleep, or nap, may be induced by administration of the nutraceutical formulation/composition presented in Table 4.

TABLE 4

Nap/Short Duration Sleep Enhancing Nutraceutical 2

| Ingredient | Grams Per 0.25 milliliter Dose |
|---|---|
| Magnesium Chloride | ≈0.0000000607899506838612 0 |
| Sodium Ascorbate | ≈0.0000000911849260257918 0 |
| Potassium Carbonate | ≈0.0000000911849260257918 0 |
| Calcium Ascorbate | ≈0.0000000607899506838612 0 |
| Ascorbic Acid (ester C) | ≈0.0000005065829223655100 0 |
| Caffeine | ≈0.0000000962507552494469 0 |
| Niacin | ≈0.0000000101316584473102 0 |
| Potassium Benzoate | ≈0.0000000455924630128959 0 |
| Chromium Picolinate | ≈0.0000000001894620129647 0 |
| Chromium Polynicotinate | ≈0.0000000001894620129647 0 |
| Coenzyme Q10 | ≈0.0000000633228652956888 0 |

TABLE 4-continued

Nap/Short Duration Sleep Enhancing Nutraceutical 2

| Ingredient | Grams Per 0.25 milliliter Dose |
|---|---|
| L-Glutamine | ≈0.0000002532914611827550 0 |
| L-Arginine | ≈0.0000002532914611827550 0 |
| Potassium Sorbate | ≈0.0000000101316584473102 00 |
| Sodium Nitrite | ≈0.0000000073454523742999 00 |
| Vitamin A | ≈0.0000000010444627942921 30 |
| Vitamin B1 | ≈0.0000000001825809282692 4 |
| Vitamin B2 | ≈0.0000000001379031288661 7 |
| Vitamin B3 | ≈0.0000000017589684804358 0 |
| Vitamin B6 | ≈0.0000000017589685000138 8 |
| Vitamin B12 | ≈0.0000000000005276905441 3 |
| Vitamin C | ≈0.0000000005276905441307 41 |
| Vitamin D3 | ≈0.0000000000835570235416 70 |
| Vitamin E | ≈0.0000000000609269963324 7 |
| Vitamin H | ≈0.0000000000158307163239 2 |
| Folic Acid | ≈0.0000000000168860974107 2 |
| Copper | ≈0.0000000000773946131389 8 |
| Iron | ≈0.0000000006719259595263 8 |
| Potassium Iodide | ≈0.0000000000057784408887 6 |
| Calcium Carbonate | ≈0.0000000035179369608711 1 |
| Zinc | ≈0.0000000005663878506611 7 |

Without wishing to be bound by any particular theory, it is believed, given the components, ingredients, additives, adjuncts and the like present in the nutraceutical formulations/compositions and the extremely small dosages of such components/ingredients, etc., that the mechanism by which the nutraceutical compositions/formulations of the present technology elicit effects on sleep is not a systemic mechanism, but rather a central mechanism.

The following examples describe some of the preferred embodiments of the present technology without limiting the technology thereto. Other embodiments include, but are not limited to, those described in the above written description, including additional or alternative components, alternative concentrations, and additional or alternative properties and uses.

EXAMPLES

Example 1

Nutraceutical Composition/Formulation for Enhanced Sleep Quality and Treatment of Sleep Disorders Sleep Study Design Twelve healthy adults, 6 men and 6 women were recruited. Individuals who did not have a known or suspected sleep disorder, but reported frequent waking, difficulty falling asleep, restlessness, and/or upon waking feeling fatigued were accepted. Individuals were at least 18 years of age, generally in good health (no known cardiovascular, pulmonary, neurological, or metabolic disease), non smoker, available for four (4) consecutive nights (without a test, or significant project due), body mass index (BMI)<30, and have not previously participated in a formal sleep study. The study took place in a new suite hotel with quiet rooms. Two bedroom suites were utilized so that the sleep technician could set up equipment in the common room and conduct the sleep study on two participants at once. Each participant had his or her own room and bathroom.

On each of the four nights, the participant was asked to arrive approximately 1 hour before he or she would normally go to bed and maintain their normal schedule and routine as much as possible. Upon arrival, subjects were met by a researcher and sleep technician to undergo the preparation process. First, each subject was given a short survey to determine how he or she felt during their previous night's sleep and how the previous night's sleep affected their day's activities. Preparation further included placing EEG (electroencephalogram) sticky electrodes on the subject's chin, scalp, and the outer edge of their eyelids and ECG (electrocardiogram) sticky electrodes on the subject's chest. These small sticky electrodes remained in place while subjects slept and were used to monitor brain activity, heart activity and chin muscle activity. Respiration was measured with a light plastic wire and a thermometer positioned on the face. Elastic bands around the chest and abdomen were used to record breathing and body movement. A small attachment to a finger (pulse oximeter) was used to monitor blood oxygen content. A specially trained polysomnographic technologist prepared the subjects and was on duty throughout the overnight stay. Once the participant was properly prepared, they were instructed to go to bed and follow their normal pattern of behavior (watching TV, reading, etc.) including turning off lights at their normal bed time.

On the first night, the 12 participants received neither the nutraceutical composition/formulation presented in Table 1 nor the placebo. The subjects were monitored on the first night in order to establish a baseline polysomnography (PSG). On the subsequent three nights each subject received, in a randomized order, either 0.20 ml of the nutraceutical composition/formulation from Table 1, 0.25 ml of the nutraceutical composition/formulation from Table 1, or 0.25 ml placebo (sterilized distilled water). Multiple dosages were tested in order to bracket and identify the effective dosage range(s). Thus, upon completion of the four night study, a baseline (B), placebo (P), 0.20 milliliter nutraceutical/supplement composition/formulation (A20), and 0.25 milliliter nutraceutical composition/formulation (A25) PSG had been recorded for each subject. The liquid nutraceutical composition/formulation and placebo were administered sublingually, via a dropper under the tongue, and the subject was instructed not to swallow for 60 seconds. The participants were told only that 3 different formulations were being used and were only told about the use of the placebo at the completion of the study. Upon waking in the morning, the sleep technician removed all of the electrodes and completed a short survey (about 5 minutes) documenting the subject's sleep.

Analysis of the first sleep study results revealed that the product was most effective when administered to subjects with the poorest baseline sleep quality. Therefore a second sleep study was performed (discussed below) on individuals who suffered from moderate to severe sleep dysfunction.

The second sleep study was performed in a similar manner as described above with the following two differences: (1) The 12 subjects enlisted in the second sleep study suffered from moderate to severe sleep dysfunction (as described below), and (2) the on nights 2, 3, and 4 the subjects were administered either 0.25 milliliters of the nutraceutical composition/formulation from Table 1, 0.30 milliliters of the nutraceutical composition/formulation presented in Table 1, or 0.25 ml placebo (sterilized distilled water). Thus, upon completion of the four night study, a baseline (B), placebo (P), 0.25 milliliter nutraceutical composition/formulation (A25), and 0.30 milliliter nutraceutical composition/formulation (A30) PSG had been recorded for each subject The subjects (8 male and 4 female) were between the ages of 26 and 66 and exhibited sleep dysfunctions including the following symptoms: frequent arousals, difficulty getting to sleep initially, difficulty getting back to sleep when aroused, significant snoring, documented sleep apnea (by partner), restless sleep, tired during the day, daytime fatigue and napping. The subjects in this portion of the study also reported the use of over-the-counter medications to assist with sleep (most commonly Tylenol PM® and Benadryl®).

Ratio of Stage 1 Sleep to DELTA and REM Sleep

Figure 2:
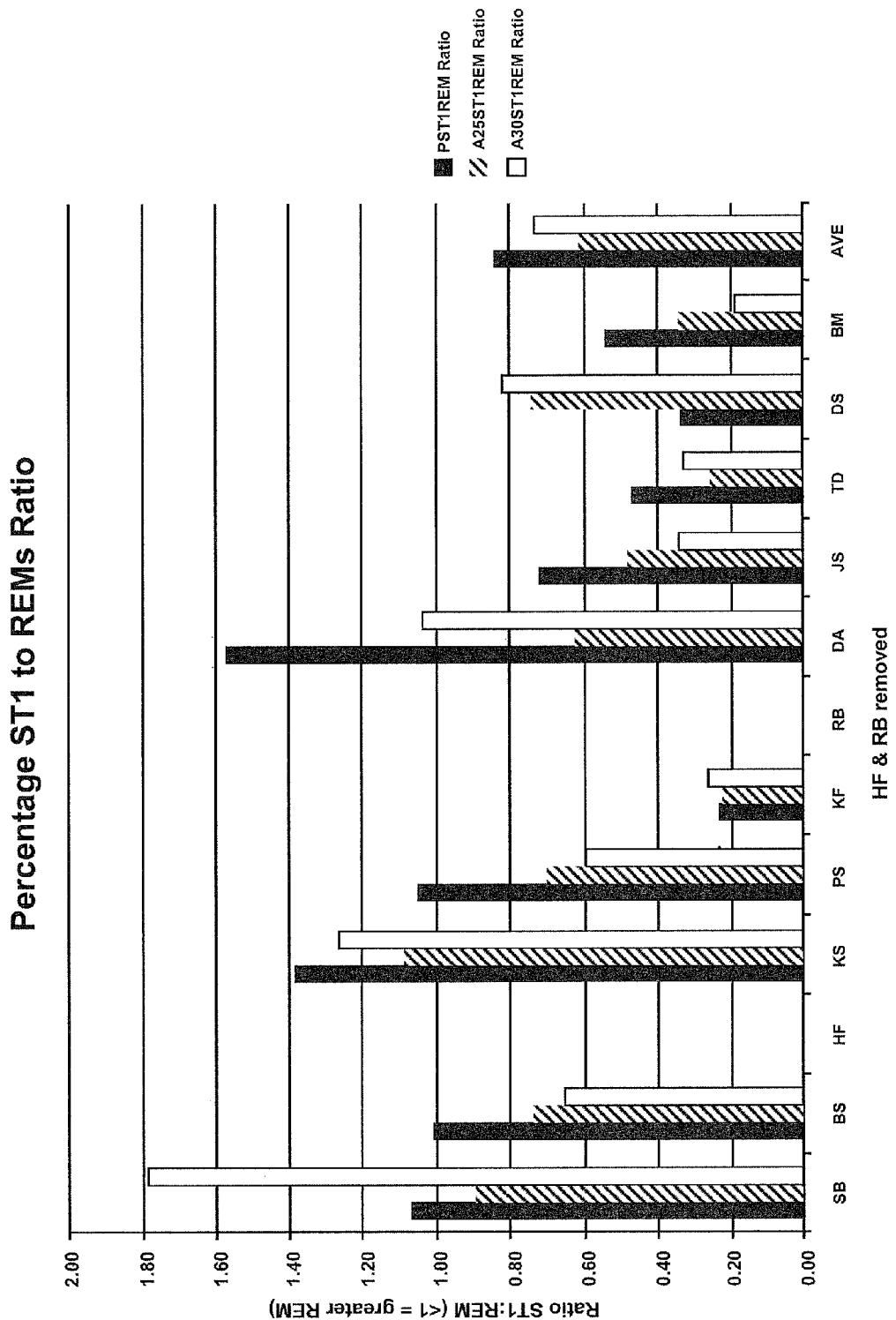
FIG. 2 is a bar graph of the ratio between stage 1 sleep percentage and REM sleep percentage for individuals who were administered placebo and the nutraceutical composition presented in Table 1.

Analysis of the results from the second sleep study revealed that when subjects received the nutraceutical composition/formulation presented in Table 1, a decreased ratio of stage 1 sleep compared to DELTA and REM sleep resulted (FIGS. 1 and 2). This ratio illustrates that in the majority of cases in which the nutraceutical composition/formulation was used there was a marked decreased in this ratio. This means that more time was spent in the restorative sleep stages of DELTA and/or REM. Two subjects were removed due to the fact that the number of minutes that they spent in DELTA and REM was negligible.

Arousals and Awakenings

Figure 3:
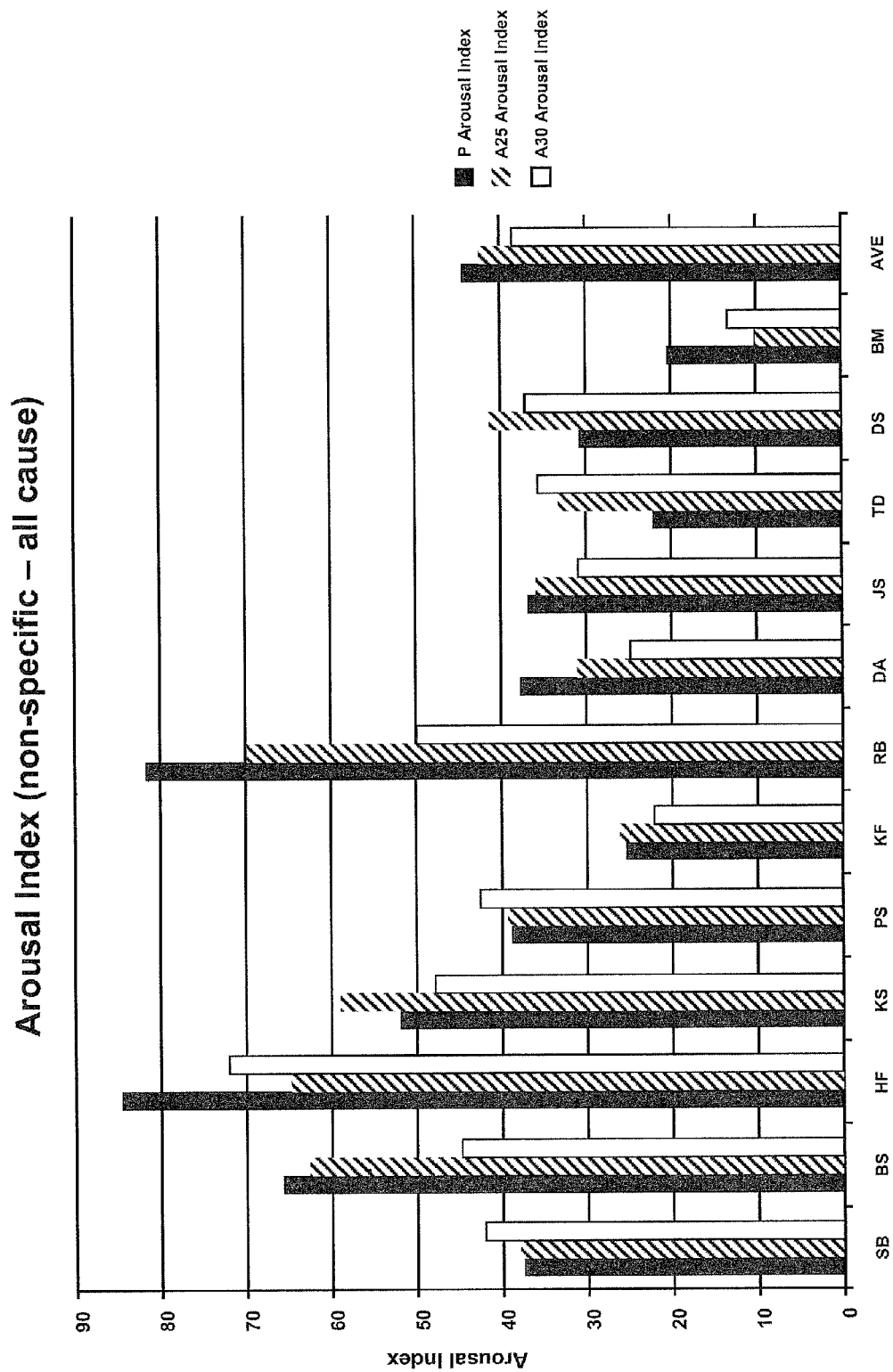
FIG. 3 is a bar graph of the all cause non-specific arousal indices of individuals who were administered placebo and the nutraceutical composition presented in Table 1.
Figure 4:
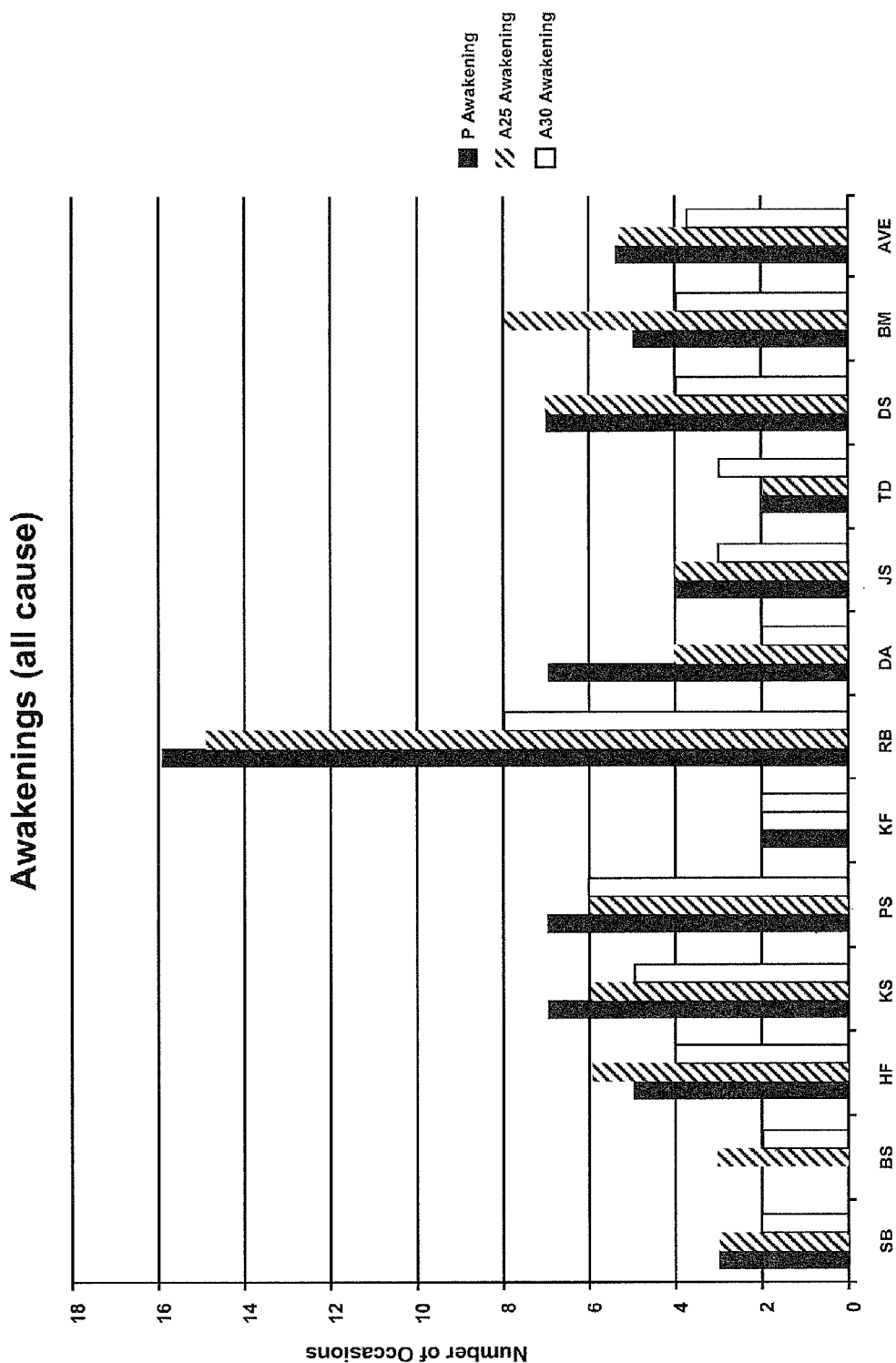
FIG. 4 is a bar graph of the awakenings of individuals who were administered placebo and the nutraceutical composition presented in Table 1.
Figure 5:
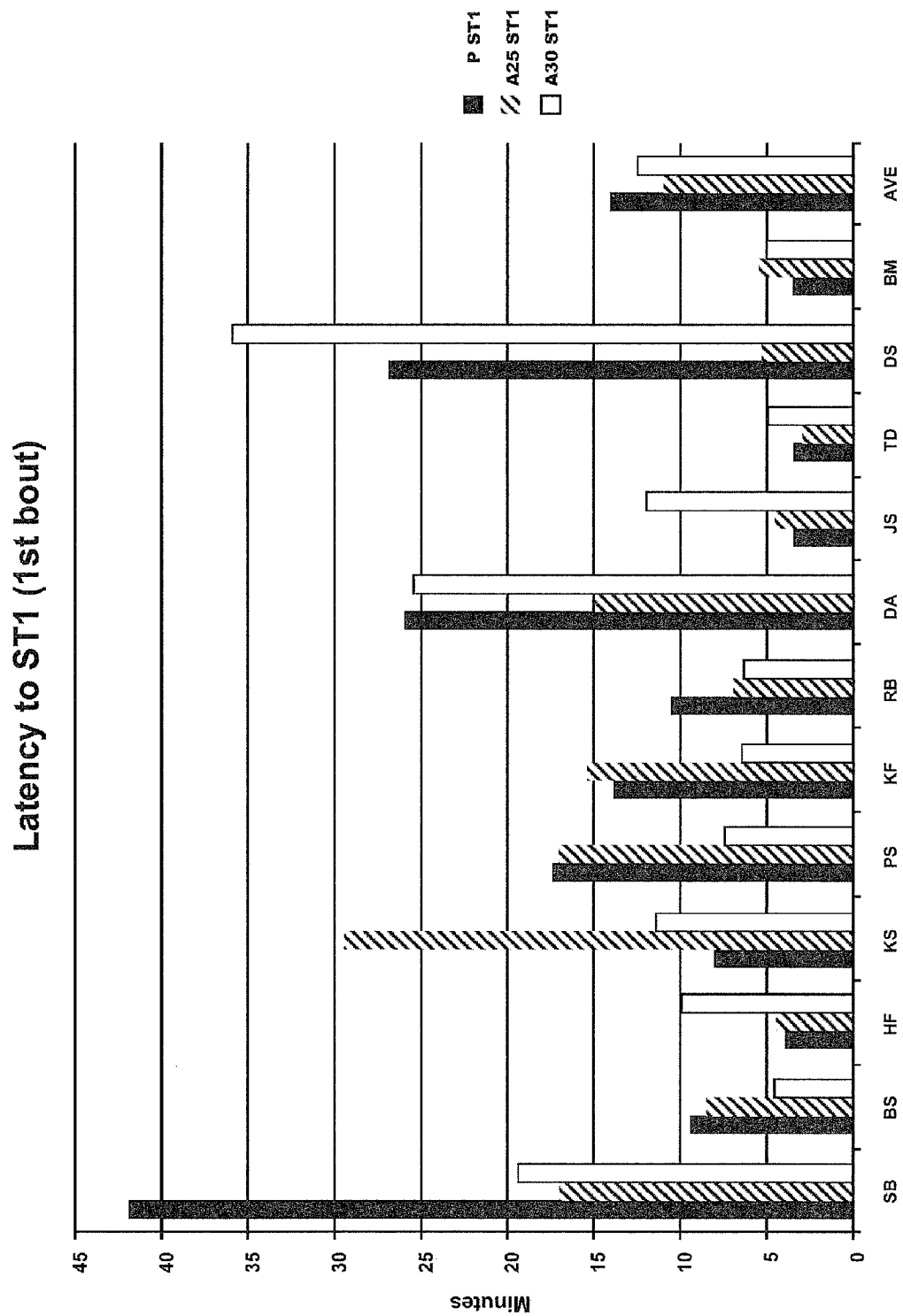
FIG. 5 is a bar graph of the latency to stage 1 sleep of individuals who were administered placebo and the nutraceutical composition presented in Table 1.
Figure 6:
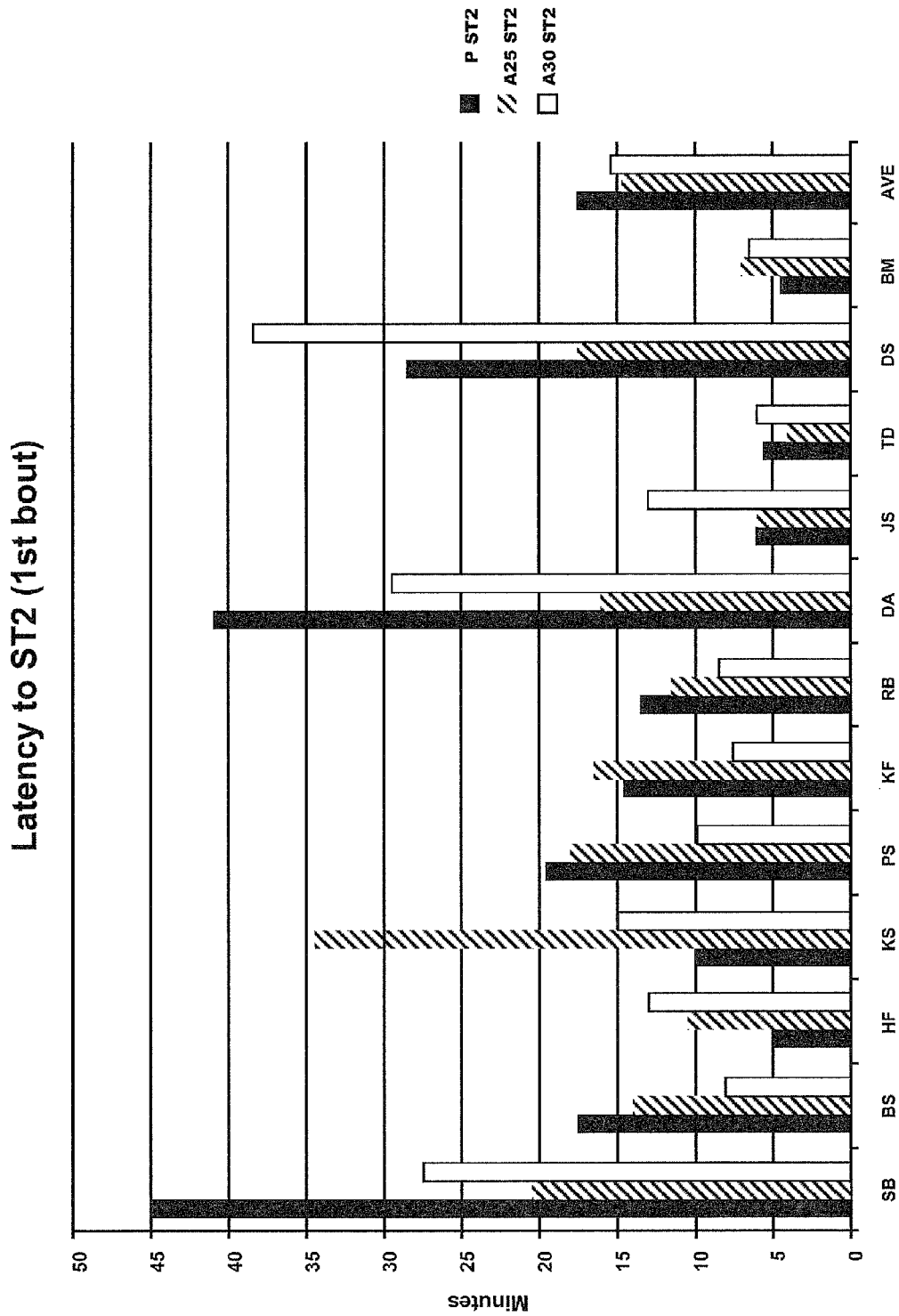
FIG. 6 is a bar graph of the latency to stage 2 sleep of individuals who were administered placebo and the nutraceutical composition presented in Table 1.
Figure 7:
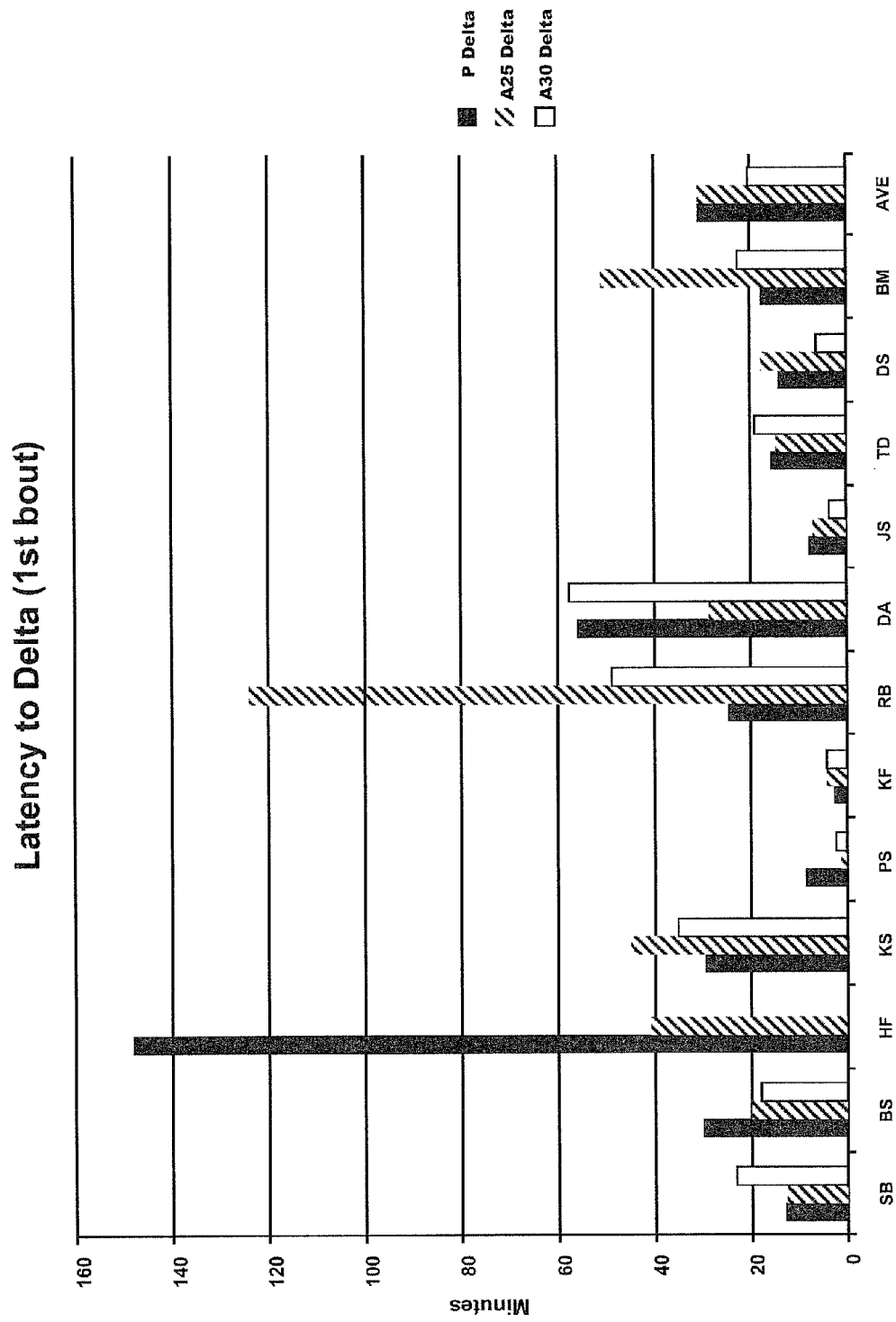
FIG. 7 is a bar graph of the latency to DELTA sleep of individuals who were administered placebo and the nutraceutical composition presented in Table 1.
Figure 8:
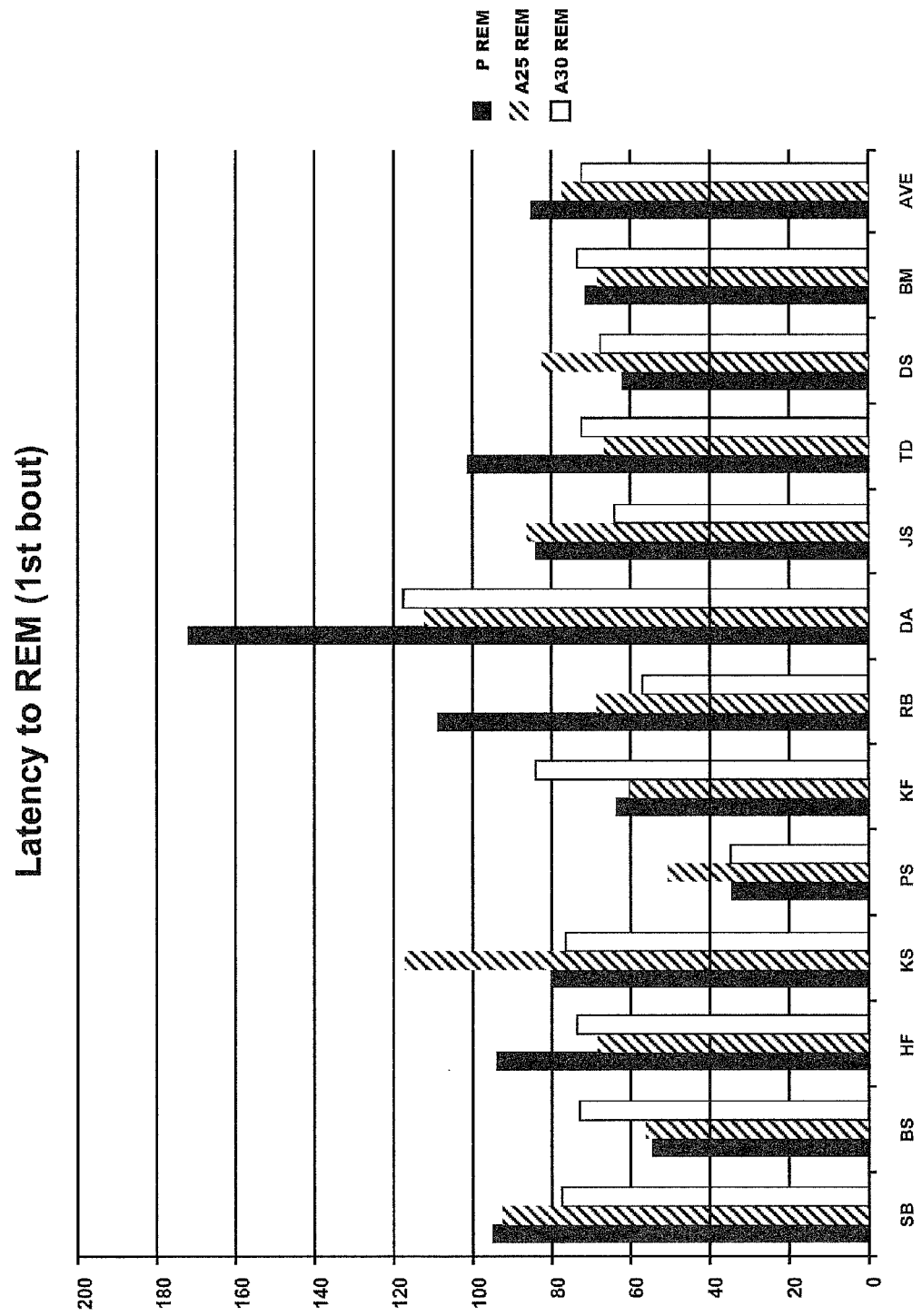
FIG. 8 is a bar graph of the latency to REM sleep of individuals who were administered placebo and the nutraceutical composition presented in Table 1.
Figure 9:
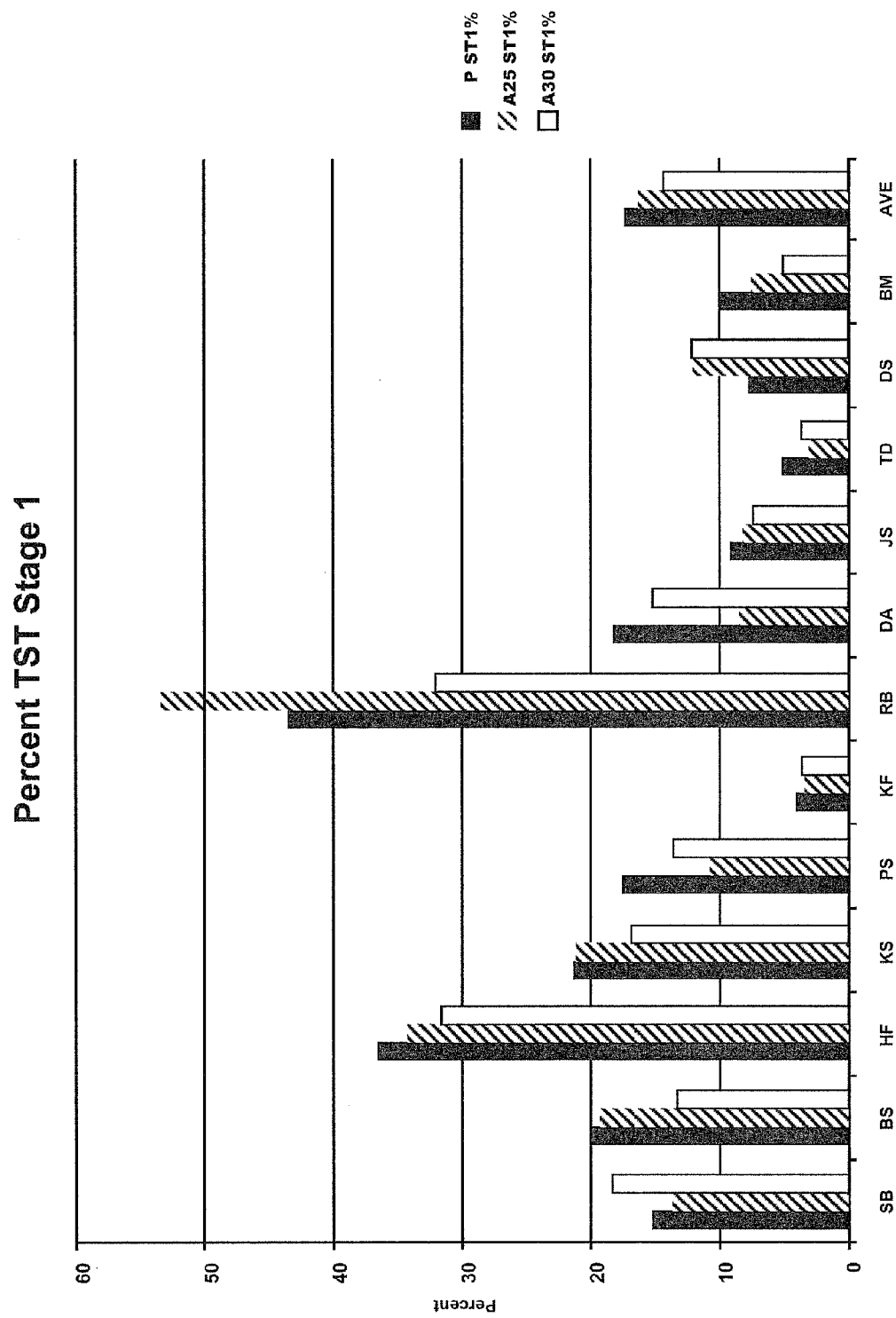
FIG. 9 is a bar graph of the percentage of total sleep time (TST) spent in stage sleep for individuals who were administered placebo and the nutraceutical composition presented in Table 1.
Figure 10:
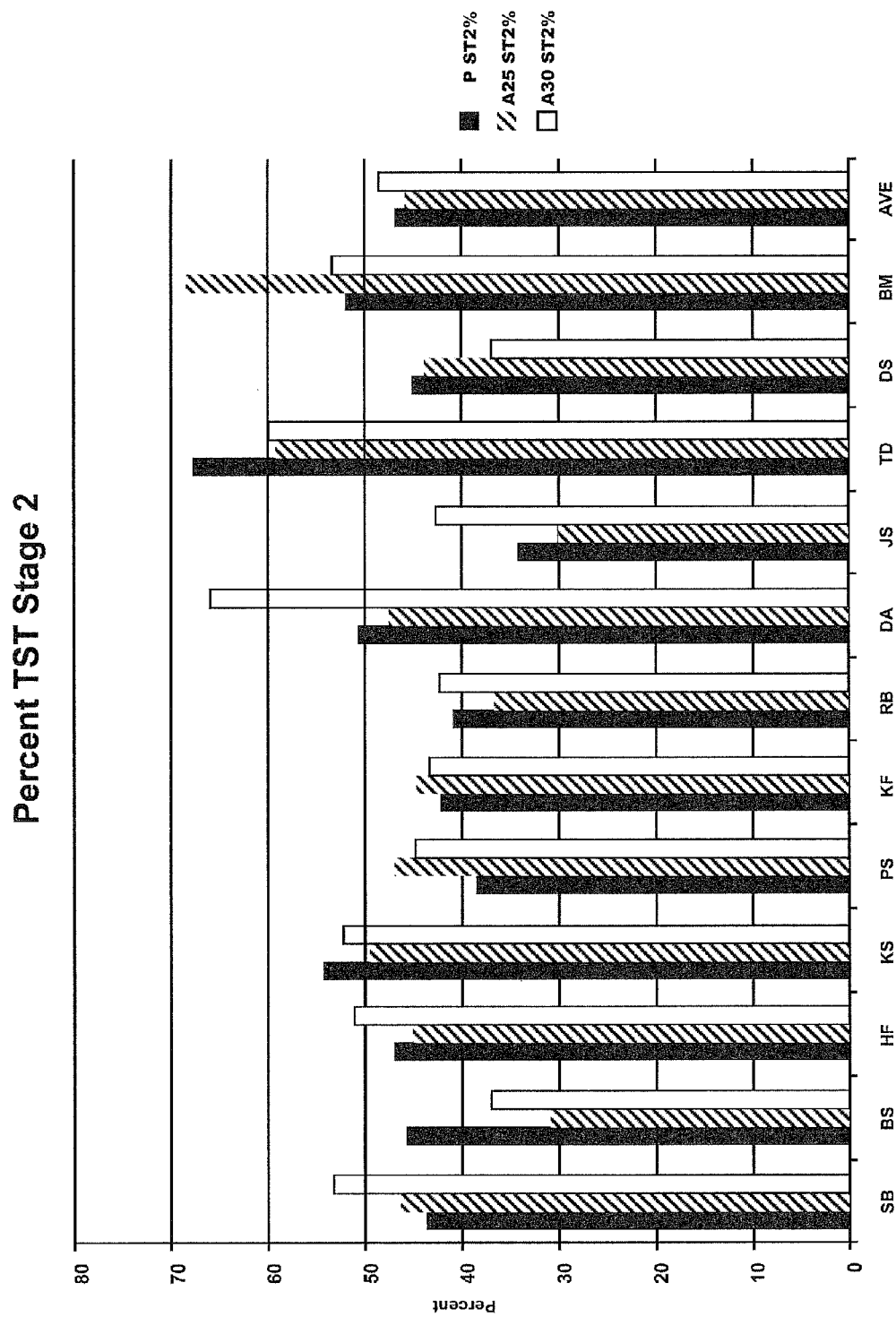
FIG. 10 is a bar graph of the percentage of total sleep time (TST) spent in stage 2 sleep for individuals who were administered placebo and the nutraceutical composition presented in Table 1.
Figure 11:
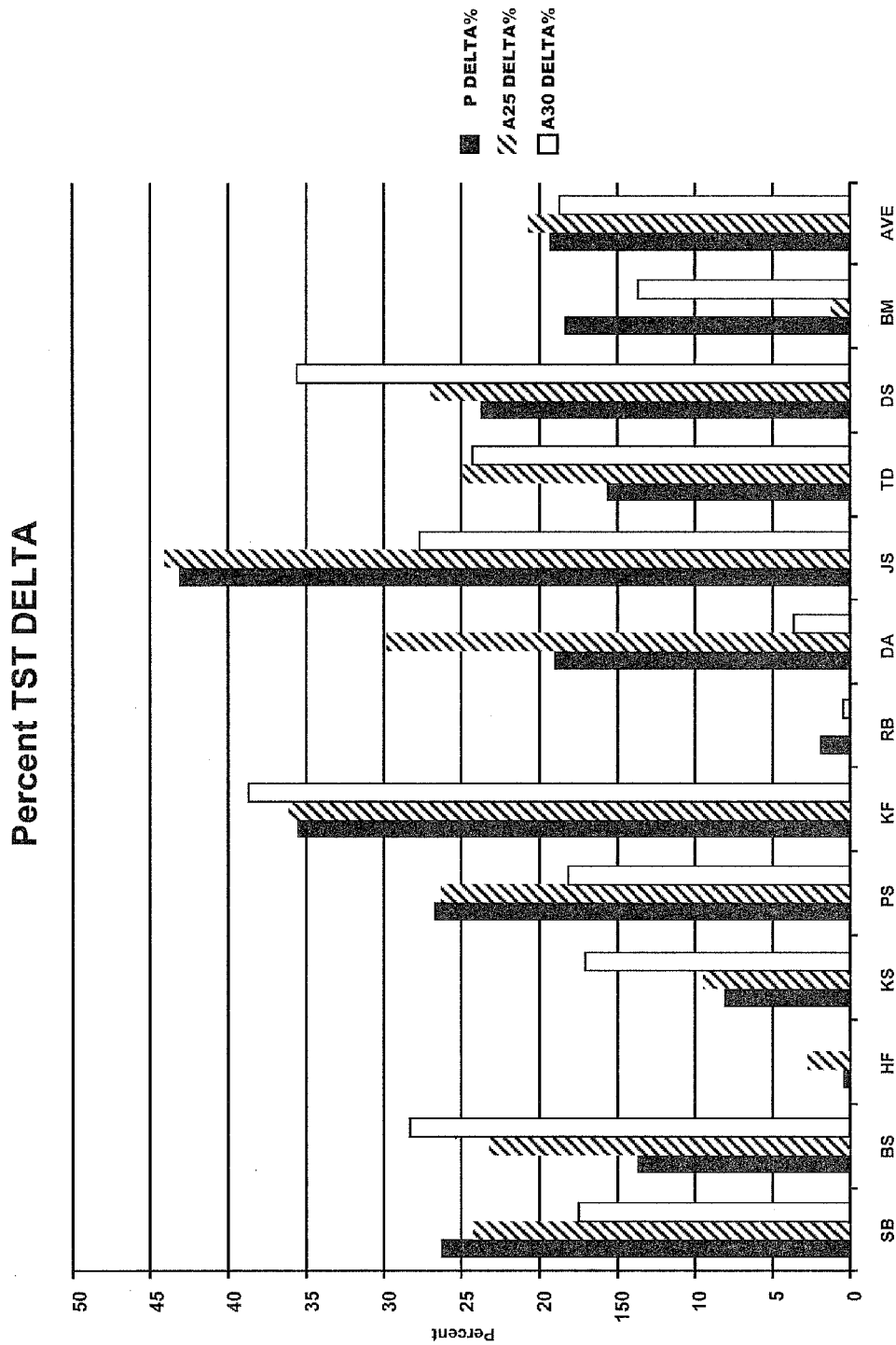
FIG. 11 is a bar graph of the percentage of total sleep time (TST) spent in DELTA sleep for individuals who were administered placebo and the nutraceutical composition presented in Table 1.
Figure 12:
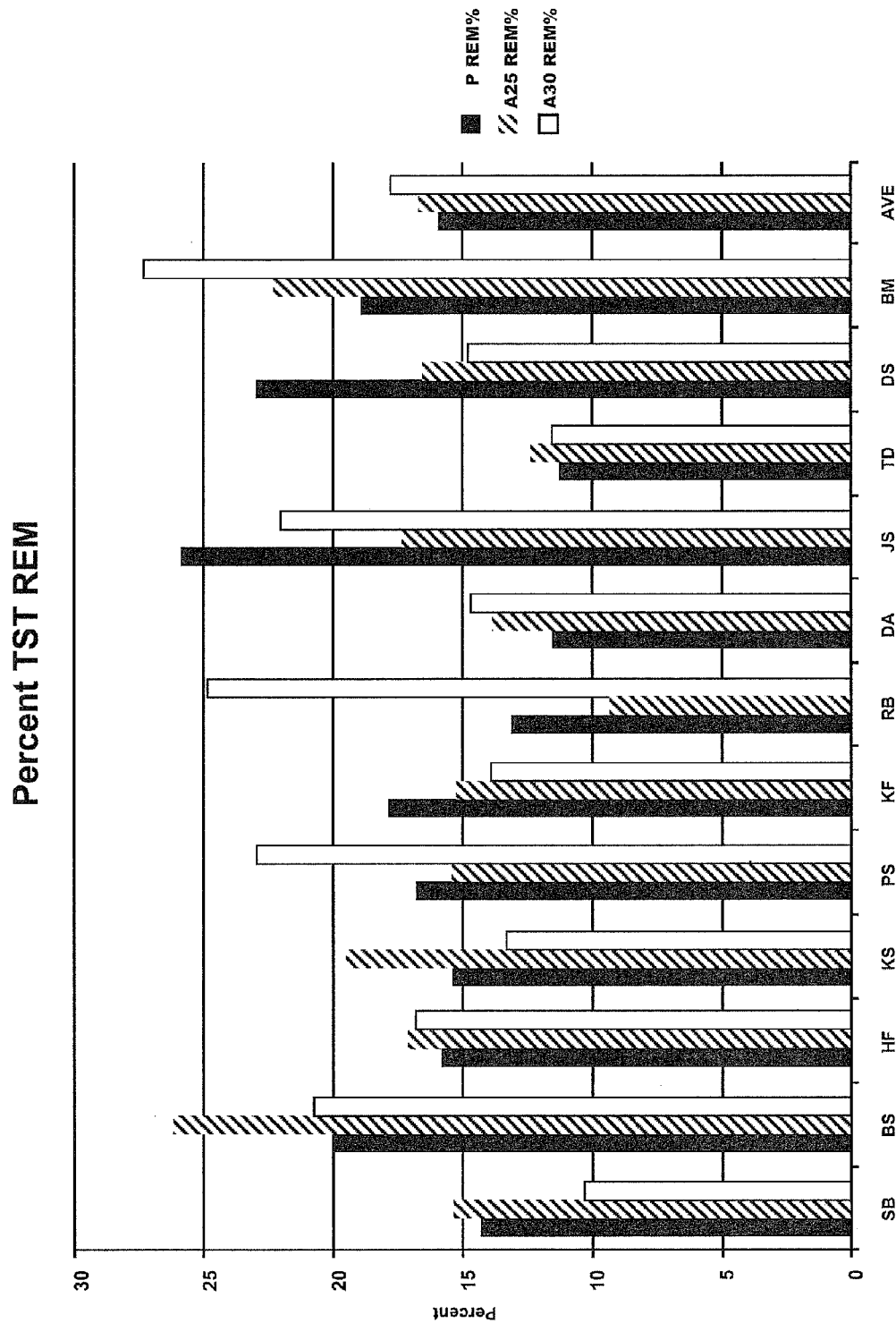
FIG. 12 is a bar graph of the percentage of total sleep time (TST) spent in REM sleep for individuals who were administered placebo and the nutraceutical composition presented in Table 1.
Figure 13:
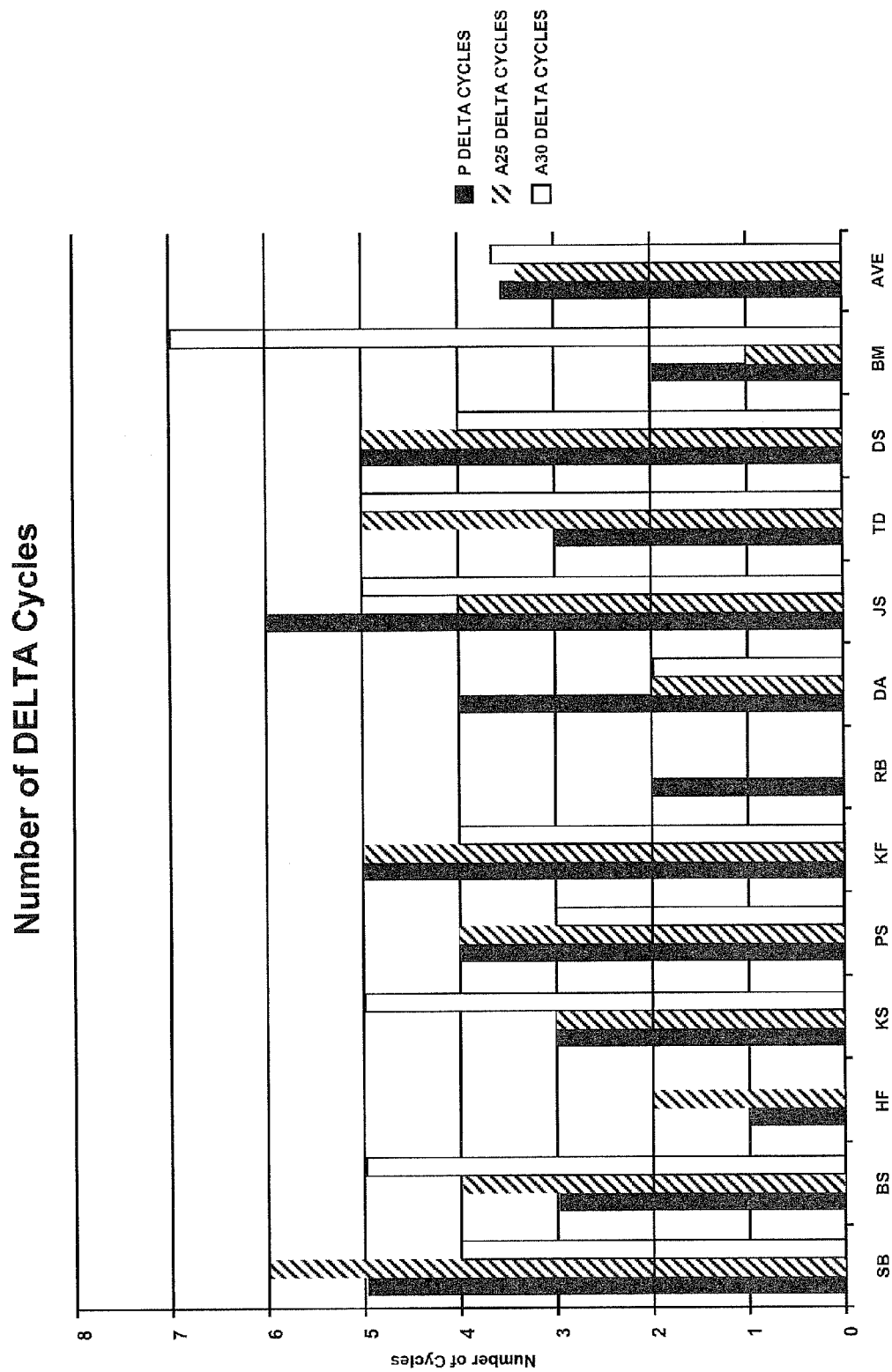
FIG. 13 is a bar graph of the number of DELTA sleep cycles for individuals who were administered placebo and the nutraceutical composition presented in Table 1.
Figure 14:
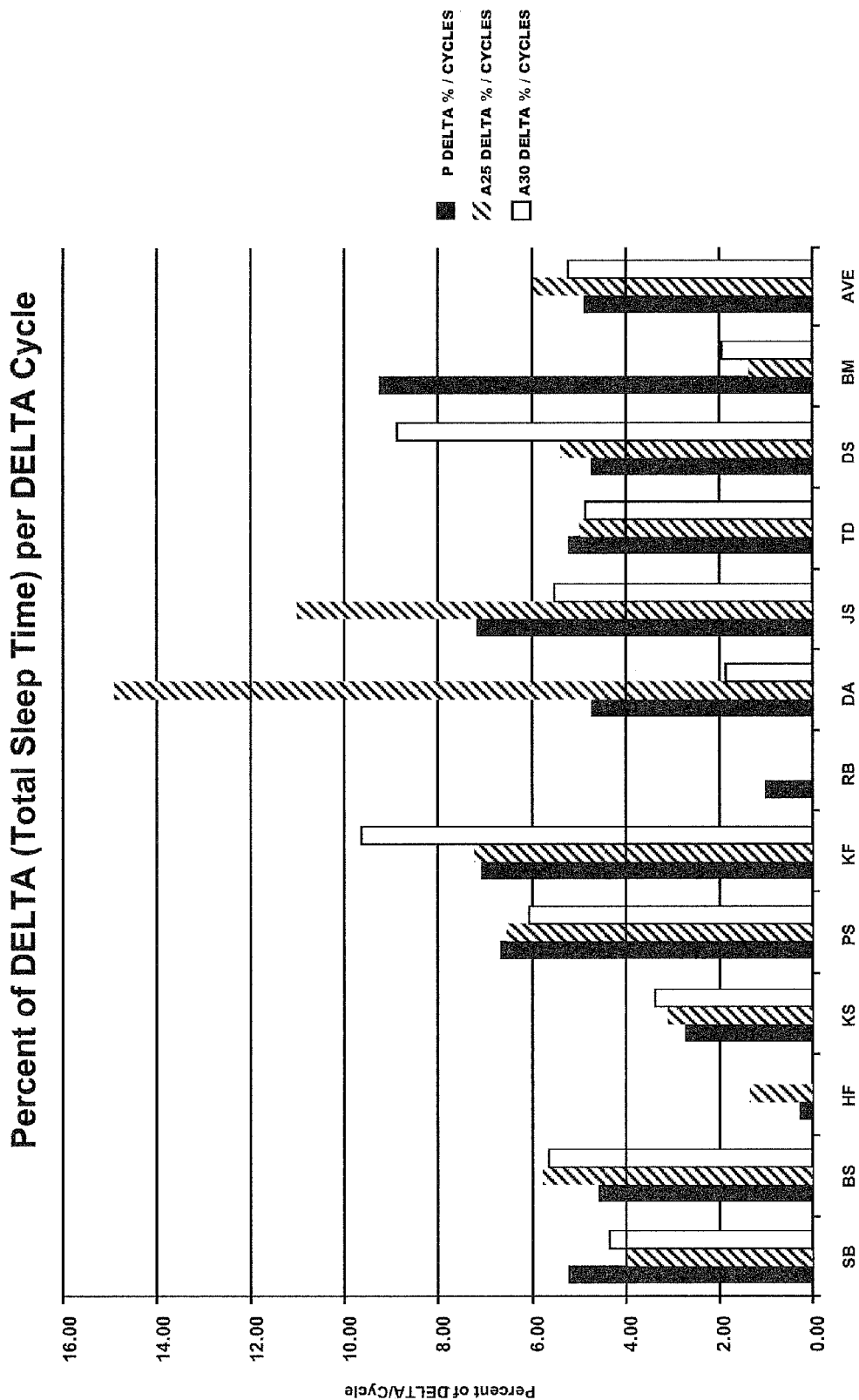
FIG. 14 is a bar graph of the percentage of DELTA sleep per DELTA cycle for individuals who were administered placebo and the nutraceutical composition presented in Table 1.
Figure 15:
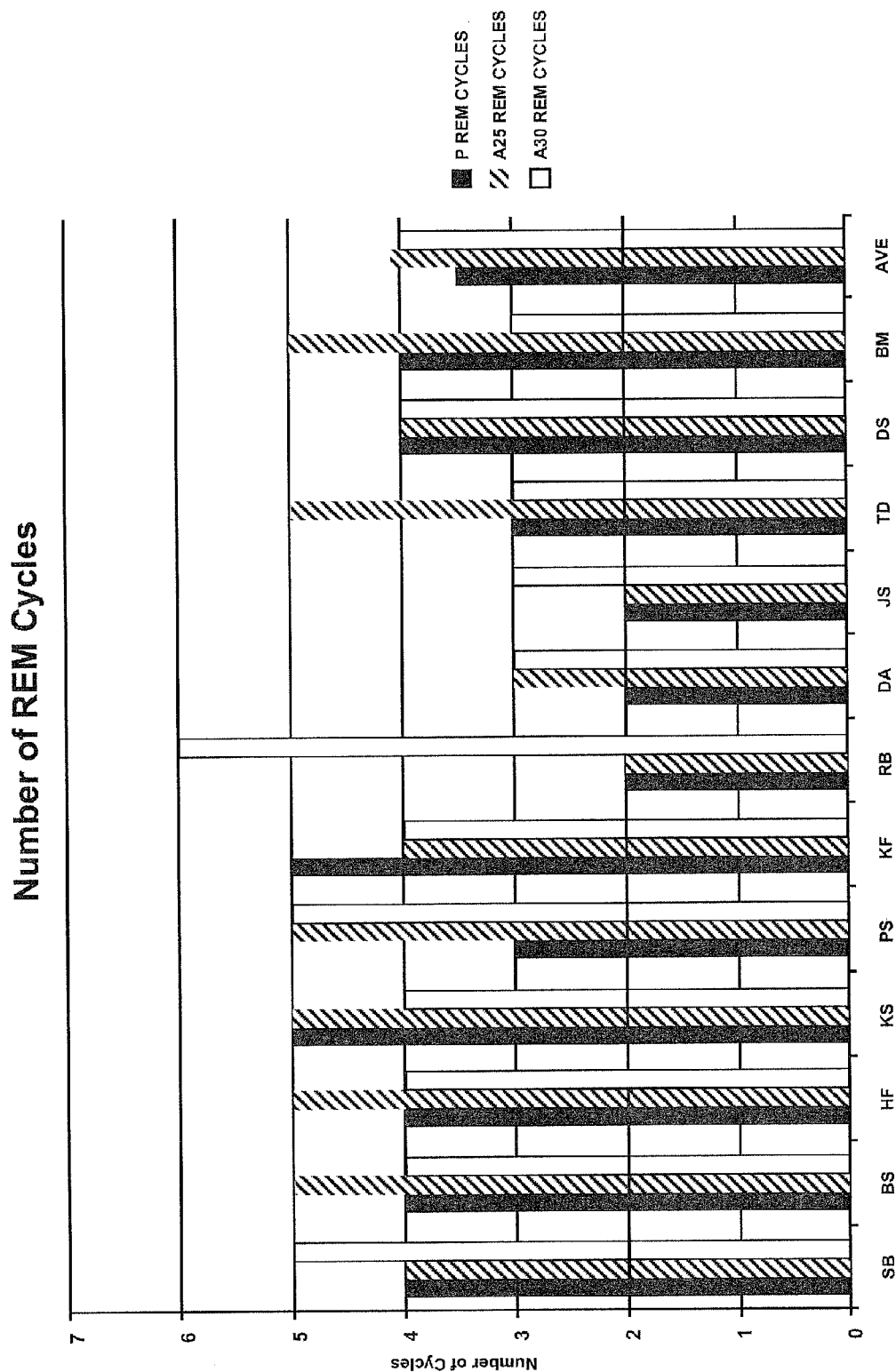
FIG. 15 is a bar graph of the number of REM sleep cycles for individuals who were administered placebo and the nutraceutical composition presented in Table 1.
Figure 16:
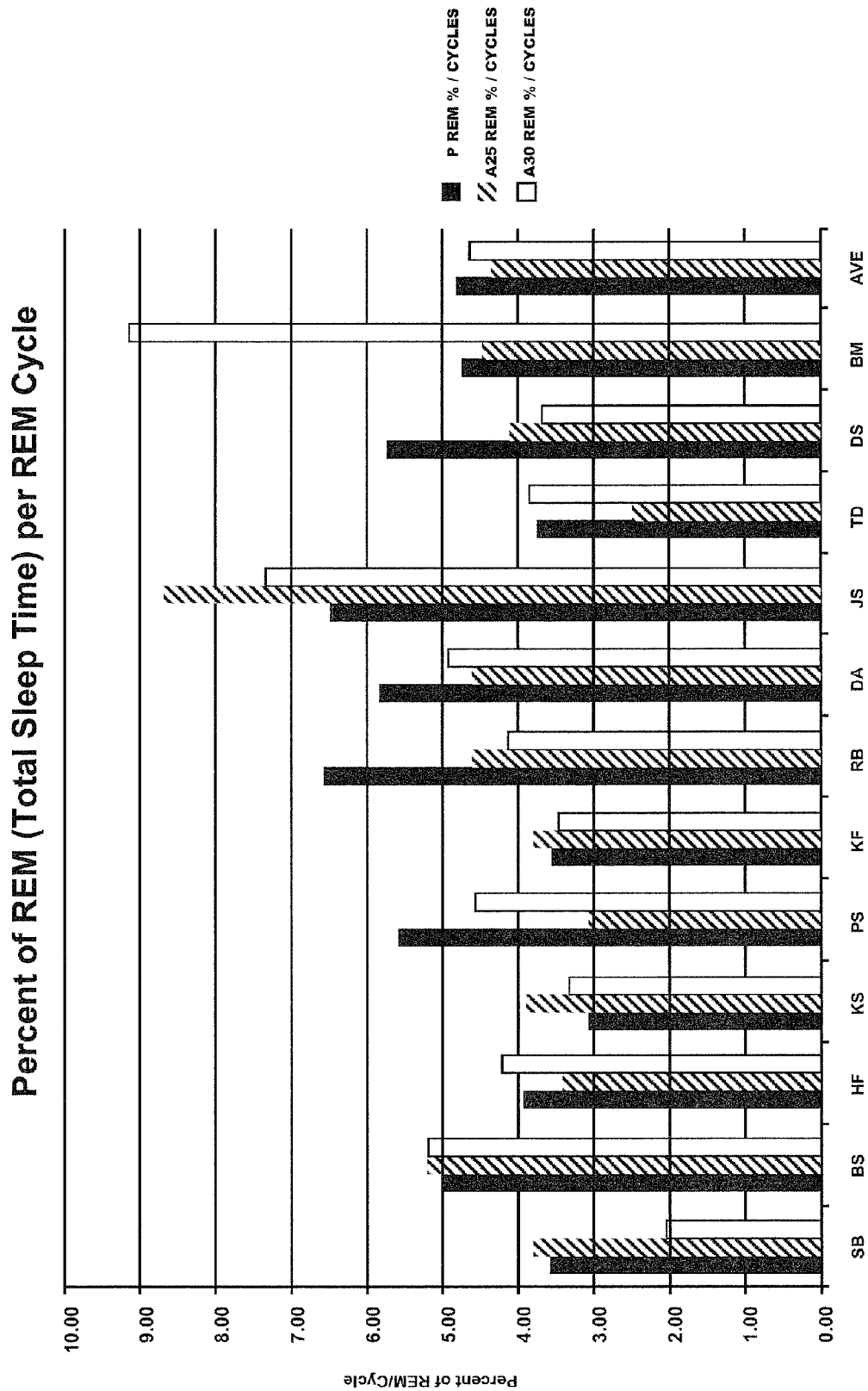
FIG. 16 is a bar graph of the percentage of REM sleep per REM cycle for individuals who were administered placebo and the nutraceutical composition presented in Table 1.

Analysis of the results from the second sleep study also revealed that when the nutraceutical composition/formulation presented in Table 1 was administered, a clear trend towards lower arousal index and fewer awakenings was observed (FIGS. 3 and 4). A large amount of inter-subject variability was also observed.

Latency

Analysis of the second sleep study results revealed some significant inter-subject variability, and a trend towards the treated subjects attaining DELTA and/or REM sleep in a lesser amount of time (decreased DELTA and REM latency) when the composition/formulation presented in Table 1 was administered (FIGS. 5 to 8).

Percentage of Total Sleep Time

Further analysis of the second sleep study data revealed a trend towards a decrease in the absolute number of minutes in Stage 1 with a corresponding increase in the number of minutes in DELTA and REM when subjects were administered the nutraceutical presented in Table 1. This is important because the longer DELTA and REM sleep stages indicate better sleep quality and more restorative sleep (FIGS. 9 to 12)

Percent of Delta and REM Per Individual Cycle of DELTA and REM

The second sleep study data also revealed that, while a great amount of inter-subject variability is present, administration of the nutraceutical presented in Table 1 appears to elicit more and longer bouts of DELTA and REM deep sleep stages. Interestingly, the subjects who demonstrated the greatest dysfunction appeared to have more and longer bouts of DELTA and REM (FIGS. 13 to 16).

Dysfunction Indices

Figure 17:
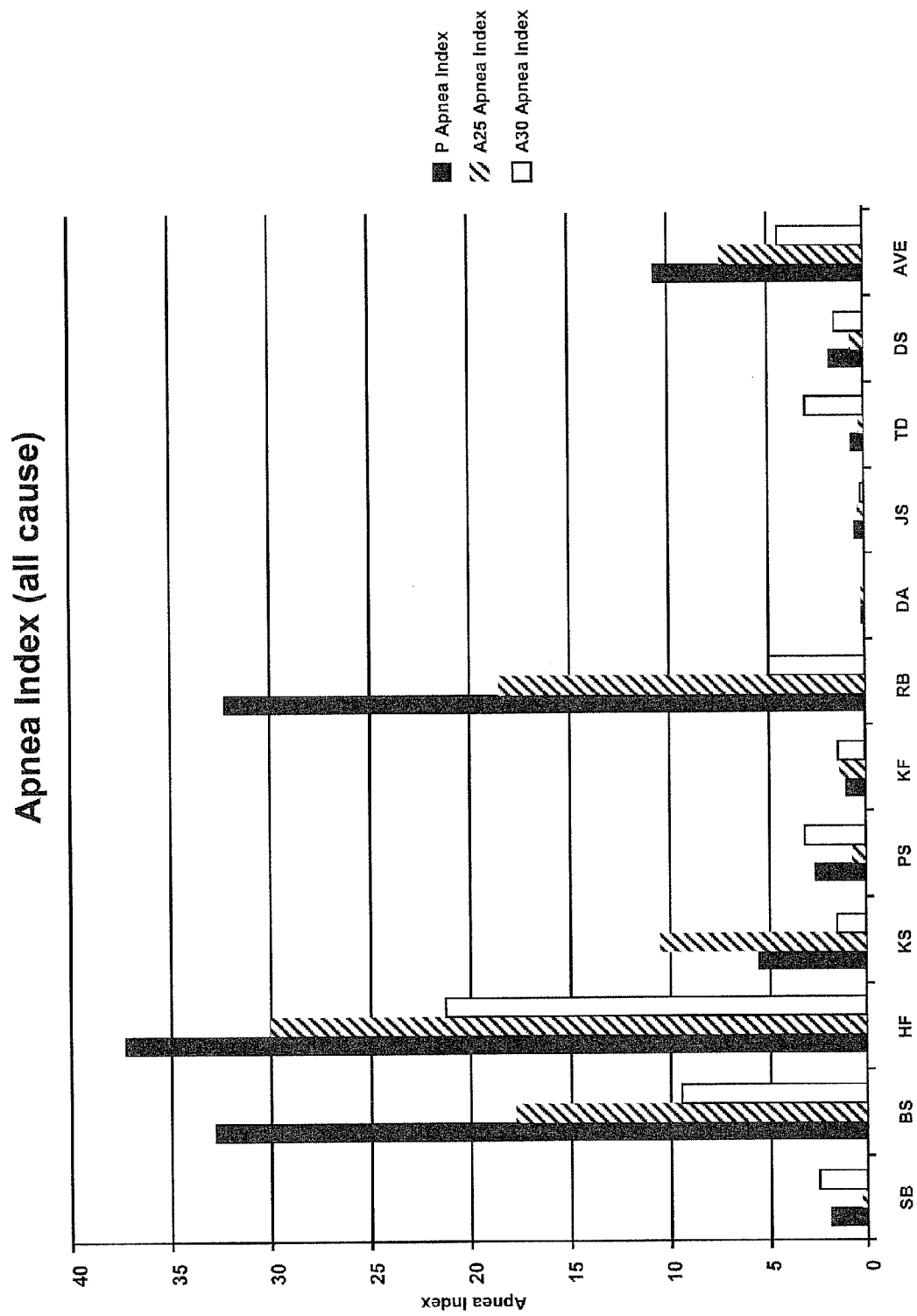
FIG. 17 is a bar graph of the apnea indices of individuals who were administered placebo and the nutraceutical composition presented in Table 1.
Figure 18:
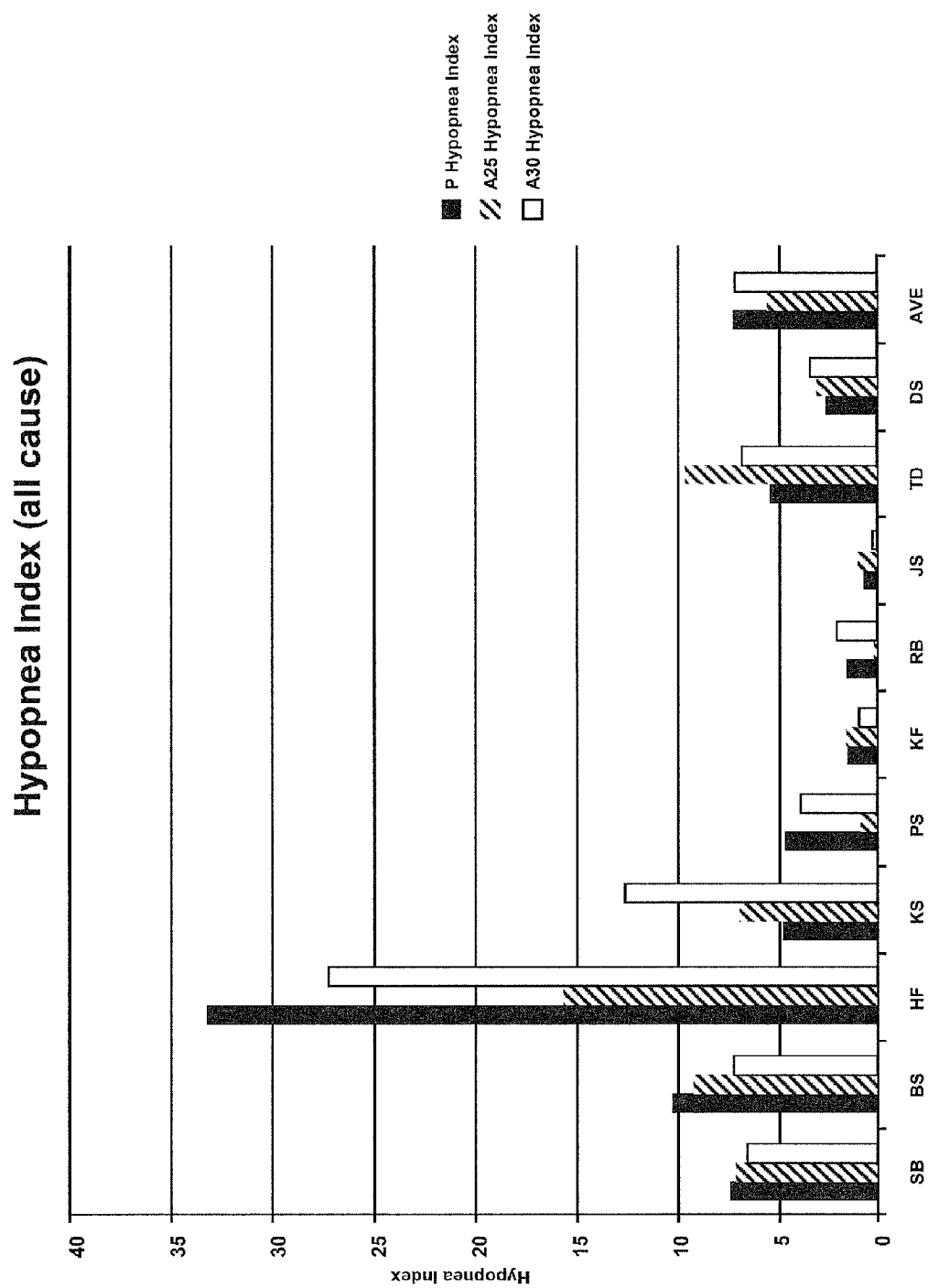
FIG. 18 is a bar graph of the hypopnea indices of individuals who were administered placebo and the nutraceutical composition presented in Table 1.
Figure 19:
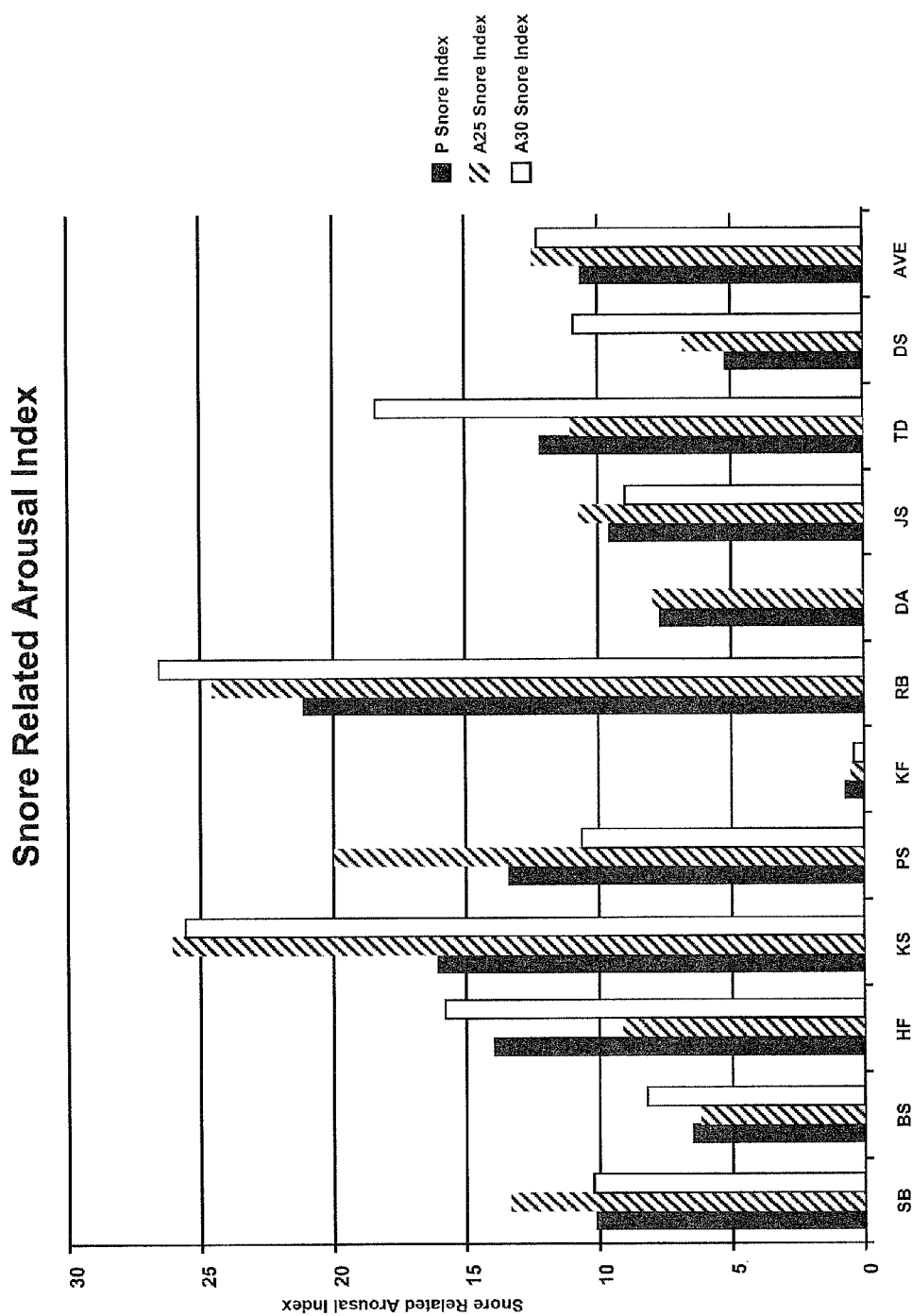
FIG. 19 is a bar graph of the snore related arousal indices of individuals who were administered placebo and the nutraceutical composition presented in Table 1.
Figure 20:
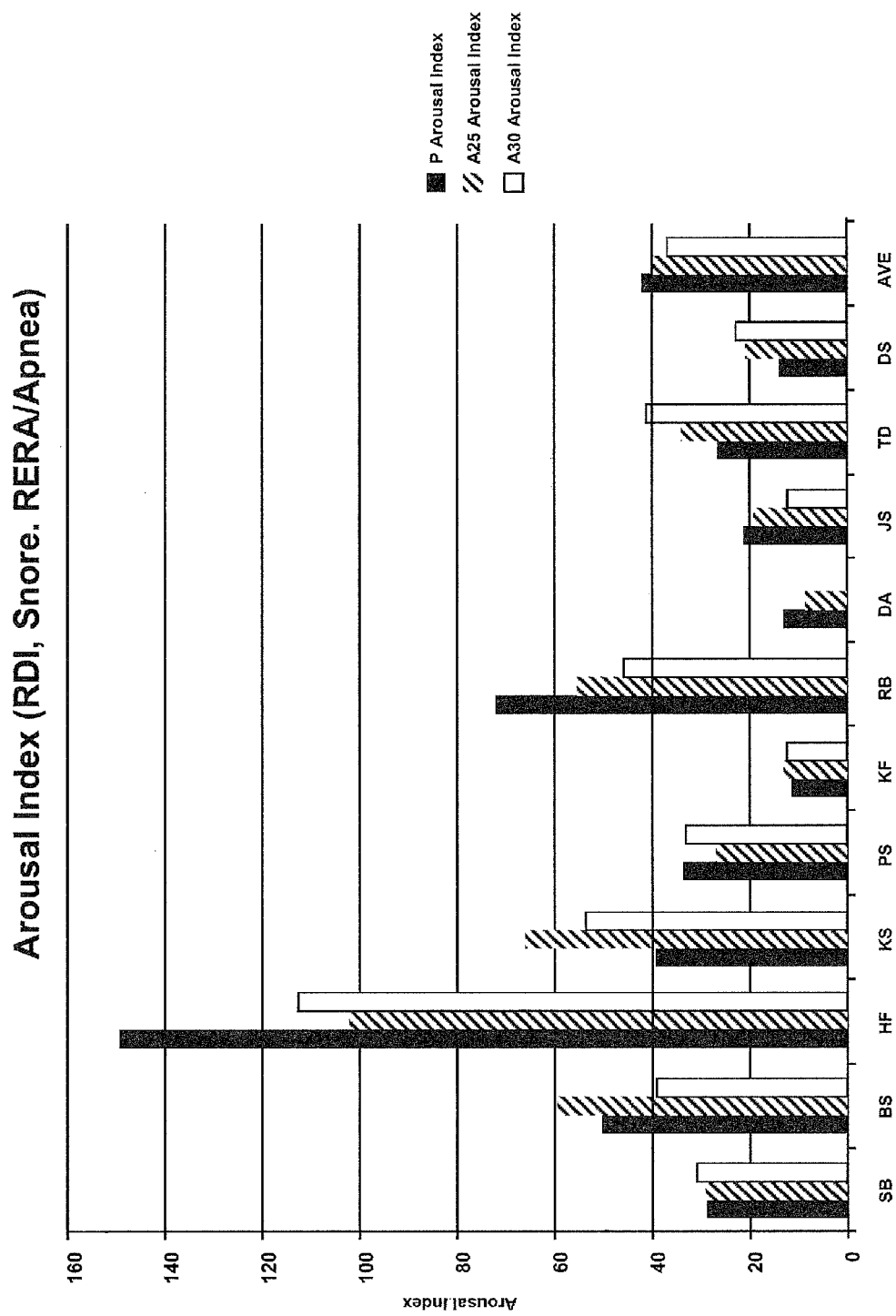
FIG. 20 is a bar graph of the arousal indices of individuals who were administered placebo and the nutraceutical composition presented in Table 1.

The Apnea Index shows that all but one of the subjects in the second study demonstrated some level of sleep apnea, while three subjects demonstrated clinical sleep apnea. The data from the three subjects with clinical sleep apnea (presented below) demonstrated drops in apneaic events. Analysis of the data also revealed, despite the inter-subject variability, that those subjects with the greatest sleep apnea issues appeared to have a positive effect from the administration of the tested nutraceutical composition/formulation presented in Table 1 (FIG. 17). This same trend is seen to a lesser degree with the Hypopnea Index and the "Combined" Arousal Index (FIGS. 18 and 20). It is evident that snoring was not effected by the product (FIG. 19).

Data for Subjects with Clinical Apnea (n=3 from Second Sleep Study)

Number of Apneas

| Subject | Placebo | A25 | A30 |
| --- | --- | --- | --- |
| BS | 197 | 119 | 61 |
| HF | 237 | 242 | 165 |
| RB | 218 | 11 | 36 |

Apnea Index

| Subject | Placebo | A25 | A30 |
| --- | --- | --- | --- |
| BS | 37.3 | 30.1 | 21.2 |
| HF | 5.5 | 10.5 | 1.3 |
| RB | 32.3 | 18 | 5 |

Number of Arousals

| Subject | Placebo | A25 | A30 |
| --- | --- | --- | --- |
| BS | 396 | 424 | 293 |
| HF | 571 | 544 | 576 |
| RB | 638 | 513 | 388 |

Arousal Index

| Subject | Placebo | A25 | A30 |
| --- | --- | --- | --- |
| BS | 65.9 | 62.8 | 45.1 |
| HF | 84.9 | 65 | 72.1 |
| RB | 81.9 | 70.3 | 50 |

Number of Awakenings

| Subject | Placebo | A25 | A30 |
| --- | --- | --- | --- |
| BS | 0 | 3 | 2 |
| HF | 5 | 6 | 4 |
| RB | 16 | 15 | 8 |

Latency to First Bout in minutes (ST1/ST2/DELTA/REM)

| Subject | Placebo | A25 | A30 |
| --- | --- | --- | --- |
| BS | 9.5/17.5/30/55 | 8.5/14/20/56.5 | 4.5/8/18/73.5 |
| HF | 4/5/148.5/95 | 4.5/10.5/41/69 | 10/13/0/74.5 |
| RB | 10.5/13.5/24.5/109.5 | 7/11.5/124.5/69.5 | 6.5/8.5/49/57.5 |

Percentage of Total Sleep Time (ST1/ST2/DELTA/REM)

| Subject | Placebo | A25 | A30 |
| --- | --- | --- | --- |
| BS | 20.2/45.9/13.9/20 | 19.4/31.1/23.3/26.2 | 13.6/37.2/28.4/20.8 |
| HF | 36.7/47.2/0.3/15.9 | 34.6/45.3/2.8/17.2 | 31.8/51.3/0.0/16.9 |
| RB | 43.6/41.2.1/13.2 | 53.6/37/0.1/9.3 | 32.2/42.4/0.5/24.9 |

Number of Cycles (DELTA/REM)

| Subject | Placebo | A25 | A30 |
| --- | --- | --- | --- |
| BS | 3/4 | 4/5 | 5/4 |
| HF | 1/4 | 2/5 | 0/4 |
| RB | 2/2 | 0/2 | 0/6 |

$SaO_2$ (Number of minutes <89%)

| Subject | Placebo | A25 | A30 |
| --- | --- | --- | --- |
| BS | 9 | 3.6 | 2 |
| HF | 16.7 | 12.6 | 11.3 |
| RB | 0 | 0 | 0 |

Total Sleep Time Ratio ST1/DELTA (<1 better)

| Subject | Placebo | A25 | A30 |
| --- | --- | --- | --- |
| BS | 1.45 | 0.83 | 0.48 |
| HF | 0* | 0 | 0 |
| RB | 0* | 0 | 0 |

*Absent to minimal DELTA

Total Sleep Time Ratio ST1/REM (<1 better)

| Subject | Placebo | A25 | A30 |
| --- | --- | --- | --- |
| BS | 1.01 | 0.74 | 0.65 |
| HF | 2.31 | 2.01 | 1.88 |
| RB | 3.30 | 5.76 | 1.29 |

While statistical analysis is not appropriate for a n=3, it is demonstrated that for the majority of the variables assessed for the three individuals with clinically documented apnea showed clinically important improvements with the introduction of the nutraceutical presented in Table 1 versus the placebo. In particular, note the decreased number of apneas and change in the apnea index. Two of the three subjects experienced a decrease in the number of arousals, and a decrease in the arousal index. It is also important to note the varying dosage related effects.

Statistics

A statistical analysis was performed with the 6 subjects from the first study who exhibited the highest level of sleep dysfunction together with all 12 of the subjects from the second study (n=18, dose bracket from A20 to A25). The following statistical terms are defined herein as follows: "n" is the number of subjects included in the statistical analysis, "mean" is the sum of a list of numbers, divided by the number of numbers in the list, "variance" is the square of the standard deviation of the numbers in the list, "df" is the number of degrees of freedom, and "p" is the p value of the null hypothesis given the data is the smallest significance level p for which any of the tests would have rejected the null hypothesis.

| Ratio of the Percentage of Total Sleep Time in Stage I to REM (<1 is better) | | | | |
|---|---|---|---|---|
| | n** | mean | Variance | df | p |
| Placebo | 16 | 0.969 | 0.50 | 15 | 0.036* (p ≤ 0.05) |
| A25 | 16 | 0.600 | 0.09 | | |

*Statistically significant.
**Two subjects removed from statistical analysis due to minimal or absent REM.

| Number of Apneas | | | | |
|---|---|---|---|---|
| | n*** | mean | Variance | df | p |
| Placebo | 11 | 68.18 | 230.50 | 10 | 0.243 |
| A25 | 11 | 52.73 | 106.32 | | |

***The six subjects from the first study who exhibited the highest level of sleep dysfunction and one subject from the second sleep study were removed from statistical analysis due to minimal or absent apneaic events.

| Apnea Index | | | | |
|---|---|---|---|---|
| | n**** | mean | Variance | df | p |
| Placebo | 11 | 10.67 | 230.50 | 10 | 0.109 |
| A25 | 11 | 7.33 | 106.32 | | |

****The six subjects from the first study who exhibited the highest level of sleep dysfunction and one subject from the second sleep study were removed from statistical analysis due to minimal or absent apneaic events.

| Number of Arousals | | | | |
|---|---|---|---|---|
| | n | mean | Variance | df | p |
| Placebo | 18 | 270.44 | 21095.09 | 17 | 0.177 |
| A25 | 18 | 248.44 | 20803.91 | | |

| Arousal Index | | | | |
|---|---|---|---|---|
| | n | mean | Variance | df | p |
| Placebo | 18 | 40.27 | 393.92 | 17 | 0.129 |
| A25 | 18 | 36.78 | 299.50 | | |

| Combined Arousal Index | | | | |
|---|---|---|---|---|
| | n***** | mean | Variance | df | p |
| Placebo | 12 | 47.23 | 1883.56 | 11 | 0.274 |
| A25 | 12 | 39.93 | 730.25 | | |

*****Statistical analysis performed on twelve subjects from study 2.

| Latency to First Bout REM (min) | | | | |
|---|---|---|---|---|
| | n | mean | Variance | df | p |
| Placebo | 18 | 96.86 | 3729.73 | 17 | 0.099 |
| A25 | 18 | 82.06 | 1100.20 | | |

| Latency to First Bout DELTA (min) | | | | |
|---|---|---|---|---|
| | n | mean | Variance | df | p |
| Placebo | 18 | 27.31 | 1079.48 | 17 | 0.915 |
| A25 | 18 | 26.33 | 792.27 | | |

| Percent of Total Sleep Time DELTA | | | | |
|---|---|---|---|---|
| | n | mean | Variance | df | p |
| Placebo | 18 | 20.31 | 137.15 | 17 | 0.069 |
| A25 | 18 | 23.57 | 166.50 | | |

| Percent of Total Sleep Time REM | | | | |
|---|---|---|---|---|
| | n | mean | Variance | df | p |
| Placebo | 18 | 15.69 | 15.90 | 17 | 0.120 |
| A25 | 18 | 17.59 | 20.74 | | |

| Ratio of the Percentage of Total Sleep Time in Stage I to DELTA (<1 is better) | | | | |
|---|---|---|---|---|
| | n****** | mean | Variance | df | p |
| Placebo | 15 | 0.923 | 1.32 | 14 | 0.097 |
| A25 | 15 | 0.515 | 0.29 | | |

******Three subjects were removed from statistical analysis due to minimal or absent DELTA.

One variable (Ratio of the Percentage of Total Sleep Time in Stage 1 to REM) demonstrates a significant difference in that administration of the nutraceutical from Table 1 induced a decrease of the amount of Stage 1 sleep relative to REM sleep. In addition, the mean differences between the other variables demonstrate that administration of the nutraceutical composition/formulation presented in Table 1 elicits a trend towards clinical effectiveness for enhancing sleep quality.

An additional statistical analysis was performed with the twelve subjects from the second study (n=12, dose bracket from A25 to A30).

| Number of Apneas | | | | |
|---|---|---|---|---|
| | n* | mean | Variance | df | p |
| Placebo | 11 | 68.18 | 9347.56 | | |
| A25 | 11 | 52.73 | 6116.81 | 10 | 0.243 |
| A30 | 11 | 31.81 | 2248.56 | 10 | 0.096 |

*One subject (BM) was removed from statistical analysis due to minimal or absent apneaic events.

| Apnea Index | | | | |
|---|---|---|---|---|
| | n* | mean | Variance | df | p |
| P | 11 | 10.67 | 230.50 | | |
| A25 | 11 | 7.33 | 106.32 | 10 | 0.109 |
| A30 | 11 | 4.48 | 37.58 | 10 | 0.085 |

*One subject (BM) was removed from statistical analysis due to minimal or absent apneaic events.

Number of Arousals

|   | n | mean | Variance | df | p |
|---|---|------|----------|----|----|
| P | 12 | 303.75 | 25977.48 | | |
| A25 | 12 | 296.83 | 23663.42 | 11 | 0.717 |
| A30 | 12 | 269.00 | 16397.27 | 11 | 0.191 |

Arousal Index

|   | n | mean | Variance | df | p |
|---|---|------|----------|----|----|
| P | 12 | 44.60 | 486.45 | | |
| A25 | 12 | 42.81 | 321.13 | 11 | 0.516 |
| A30 | 12 | 38.78 | 232.64 | 11 | 0.138 |

Combined Arousal Index

|   | n* | mean | Variance | df | p |
|---|----|------|----------|----|----|
| P | 11 | 47.23 | 2071.91 | | |
| A25 | 11 | 39.93 | 803.37 | 10 | 0.318 |
| A30 | 11 | 37.10 | 904.25 | 10 | 0.180 |

*One subject (BM) was removed from statistical analysis due to minimal or absent apneaic events.

Latency to First Bout REM (min)

|   | n | mean | Variance | df | p |
|---|---|------|----------|----|----|
| Placebo | 12 | 85.63 | 1205.01 | | |
| A25 | 12 | 77.96 | 453.79 | 11 | 0.359 |
| A30 | 12 | 73.17 | 358.65 | 11 | 0.104 |

Percent of Total Sleep Time DELTA (min)

|   | n | mean | Variance | df | p |
|---|---|------|----------|----|----|
| Placebo | 12 | 19.49 | 162.40 | | |
| A25 | 12 | 20.86 | 202.61 | 11 | 0.532 |
| A30 | 12 | 18.85 | 166.04 | 11 | 0.832 |

Percent of Total Sleep Time REM

|   | n | mean | Variance | df | p |
|---|---|------|----------|----|----|
| Placebo | 12 | 15.98 | 12.59 | | |
| A25 | 12 | 16.77 | 19.75 | 11 | 0.478 |
| A30 | 12 | 17.85 | 31.12 | 11 | 0.304 |

Ratio of the Percentage of Total Sleep Time in Stage I to DELTA (<1 is better)

|   | n** | mean | Variance | df | p |
|---|-----|------|----------|----|----|
| Placebo | 8 | 0.786 | 0.71 | | |
| A25 | 8 | 0.616 | 0.50 | 7 | 0.083 |
| A30 | 8 | 0.517 | 0.14 | 7 | 0.299 |

**Four subjects were removed from statistical analysis due to minimal or absent DELTA.

Ratio of the Percentage of Total Sleep Time in Stage I to REM (<1 is better)

|   | n*** | mean | Variance | df | p |
|---|------|------|----------|----|----|
| Placebo | 10 | 0.840 | 0.20 | | |
| A25 | 10 | 0.61 | 0.08 | 9 | 0.057 ($p \leq 0.05$) |
| A30 | 10 | 0.73 | 0.26 | 9 | 0.418 |

***Two subjects were removed from statistical analysis due to minimal or absent REM.

While no variable from this analysis demonstrates a significant difference, the mean differences between the variables illustrate that administration of the nutraceutical composition/formulation presented in Table 1 elicits a trend towards clinical effectiveness for enhancing sleep quality.

The invention has now been described in such full, clear, concise and exact terms as to enable any person skilled in the art to which it pertains, to practice the same. It is to be understood that the foregoing describes preferred embodiments and examples of the invention and that modifications may be made therein without departing from the spirit or scope of the invention as set forth in the claims.

What is claimed is:

1. A nutraceutical composition in a volume equivalent to about 0.25 milliliters in a carrier suitable for oral administration, the nutraceutical composition comprising, in combination, between about $3.61 \times 10^{-7}$ to about $5.45 \times 10^{-7}$ g magnesium chloride; between about $5.42 \times 10^{-7}$ to about $8.17 \times 10^{-7}$ g sodium ascorbate; between about $5.34 \times 10^{-7}$ to about $8.17 \times 10^{-7}$ g potassium carbonate; between about $3.61 \times 10^{-7}$ to about $5.45 \times 10^{-7}$ g calcium ascorbate; between about $5.72 \times 10^{-7}$ to about $8.62 \times 10^{-7}$ g caffeine; between about $6.02 \times 10^{-8}$ to about $9.08 \times 10^{-8}$ g niacin; between about $2.71 \times 10^{-7}$ to about $4.08 \times 10^{-7}$ g potassium benzoate; between about $1.13 \times 10^{-9}$ to about $1.70 \times 10^{-9}$ g chromium picolinate; between about $1.13 \times 10^{-9}$ to about $1.70 \times 10^{-9}$ g chromium polynicotinate; between about $3.76 \times 10^{-7}$ to about $5.67 \times 10^{-7}$ g coenzyme Q-10; between about $1.51 \times 10^{-6}$ to about $2.27 \times 10^{-6}$ g L-glutamine; between about $1.51 \times 10^{-6}$ to about $2.27 \times 10^{-6}$ g L-arginine; between about $6.02 \times 10^{-7}$ to about $9.08 \times 10^{-7}$ g potassium sorbate; between about $4.37 \times 10^{-7}$ to about $6.58 \times 10^{-7}$ g sodium nitrite; between about $6.21 \times 10^{-8}$ to about $9.36 \times 10^{-8}$ g vitamin A; between about $1.09 \times 10^{-9}$ to about $1.64 \times 10^{-9}$ g vitamin B1; between about $1.24 \times 10^{-9}$ to about $8.20 \times 10^{-9}$ g vitamin B2; between about $1.05 \times 10^{-8}$ to about $1.58 \times 10^{-8}$ g vitamin B3; between about $1.05 \times 10^{-8}$ to about $1.58 \times 10^{-8}$ g vitamin B6; between about $3.14 \times 10^{-12}$ to about $4.73 \times 10^{-12}$ g vitamin B12; between about $3.14 \times 10^{-8}$ to about $4.73 \times 10^{-8}$ g vitamin C; between about $4.97 \times 10^{-9}$ to about $7.48 \times 10^{-9}$ g vitamin D3; between about $3.62 \times 10^{-10}$ to about $5.46 \times 10^{-10}$ g vitamin E; between about $1.42 \times 10^{-10}$ to about $9.41 \times 10^{-10}$ g vitamin H; between about $1.00 \times 10^{-10}$ to about $1.51 \times 10^{-10}$ g folic acid; between about $4.60 \times 10^{-10}$ to about $6.93 \times 10^{-10}$ g copper; between about $3.99 \times 10^{-9}$ to about $6.02 \times 10^{-9}$ g iron; between about $3.44 \times 10^{-11}$ to about $5.18 \times 10^{-11}$ g potassium iodide; between about $2.09 \times 10^{-8}$ to about $3.15 \times 10^{-8}$ g calcium carbonate; and between about $3.37 \times 10^{-9}$ to about $5.07 \times 10^{-9}$ g zinc.

2. The composition of claim 1 wherein the nutraceutical is administered to an individual to induce enhanced sleep quality in the individual.

3. The composition of claim 2, wherein the induced enhanced sleep quality further comprises a decreased arousal index.

4. The composition of claim 1, wherein the nutraceutical substantially avoids first pass metabolism when administered.

5. The composition of claim 1, wherein the nutraceutical is administered to an individual to induce short duration sleep.

6. The composition of claim 5, wherein the short duration sleep lasts for about one hour or less.

7. A nutraceutical composition comprising micro- or nano-quantities of the following ingredients in an oral preparation suitable for oral administration to a person in need thereof, the ingredients comprising, in combination at least one mineral selected from the group consisting of magnesium, sodium, potassium, calcium, chromium, copper, iron and zinc, at least one vitamin selected from the group consisting of A, B1, B2, B3, B6, B12, folic acid, C, D3, E and H, at least one antioxidant, and at least one amino acid selected from the group consisting of L-glutamine and L-arginine.

8. The nutraceutical composition of claim 7, wherein the at least one mineral further comprises a chloride salt, a carbonate, an ascorbate, a nitrite, a picolinate, a polynicotinate, a benzoate or an iodide.

9. The nutraceutical composition of claim 8, wherein the at least one mineral further comprises, in combination, magnesium chloride, sodium ascorbate, sodium nitrite, potassium carbonate, calcium ascorbate, potassium benzoate, chromium picolinate, chromium polynicotinate, potassium sorbate, potassium iodide, calcium carbonate, iron, copper and zinc.

10. The nutraceutical composition of claim 9, wherein the at least one vitamin further comprises, in combination, Vitamin A, Vitamin B1, Vitamin B2, Vitamin B3, Vitamin B6, Vitamin B12, folic acid, Vitamin C, Vitamin D3, Vitamin E and Vitamin H.

11. The nutraceutical composition of claim 10, wherein the at least one antioxidant further comprises coenzyme Q-10.

12. The nutraceutical composition of claim 11, wherein the at least one amino acid further comprises, in combination L-glutamine and L-arginine.

13. A nutraceutical composition comprising, in combination, magnesium or salts thereof, sodium or salts thereof, potassium or salts thereof, calcium or salts thereof, chromium, copper, iron and zinc, vitamins A, B1, B2, B3, B6, B12, folic acid, C, D3, E and H, at least one antioxidant, L-glutamine and L-arginine, wherein each of the foregoing are present in micro- or nano-quantities in an oral preparation suitable for oral administration to a person in need thereof.

14. The nutraceutical composition of claim 13, wherein the nutraceutical is administered to an individual to induce enhanced sleep quality in the individual.

15. The nutraceutical composition of claim 13, wherein the nutraceutical composition substantially avoids first pass metabolism when administered to a person in need thereof.

16. The nutraceutical composition of claim 13, wherein the nutraceutical composition is administered to an individual to induce short duration sleep.

17. The composition of claim 16, wherein the short duration sleep lasts for about one hour or less.

* * * * *